United States Patent
Braeckmans et al.

(10) Patent No.: US 12,421,486 B2
(45) Date of Patent: Sep. 23, 2025

(54) METHOD TO INCREASE THE PERMEABILITY OF THE PLASMA MEMBRANE OF CELLS AND A STRUCTURE SUITABLE FOR USE IN SUCH METHOD

(71) Applicant: Trince BV, Ghent (BE)

(72) Inventors: Kevin Braeckmans, Lokeren (BE); Ranhua Xiong, Ghent (BE); Stefaan De Smedt, Mariakerke (BE)

(73) Assignee: Trince BV, Ghent (BE)

(*) Notice: Subject to any disclaimer, the term of this patent is extended or adjusted under 35 U.S.C. 154(b) by 679 days.

(21) Appl. No.: 17/753,868

(22) PCT Filed: Sep. 21, 2020

(86) PCT No.: PCT/EP2020/076287
§ 371 (c)(1),
(2) Date: Mar. 16, 2022

(87) PCT Pub. No.: WO2021/058430
PCT Pub. Date: Apr. 1, 2021

(65) Prior Publication Data
US 2022/0403317 A1    Dec. 22, 2022

(30) Foreign Application Priority Data
Sep. 23, 2019   (EP) .................... 19198937

(51) Int. Cl.
*C12M 1/42*      (2006.01)
*C12N 13/00*     (2006.01)
(52) U.S. Cl.
CPC ............. *C12M 35/02* (2013.01); *C12N 13/00* (2013.01)
(58) Field of Classification Search
None
See application file for complete search history.

(56) References Cited

U.S. PATENT DOCUMENTS

| 9,139,416 B2 | 9/2015 | Li et al. |
| 9,957,476 B2 | 5/2018 | Gunn-Moore et al. |

(Continued)

FOREIGN PATENT DOCUMENTS

| EP | 2272945 A1 | 1/2011 |
| WO | 2010/012816 A1 | 2/2010 |

(Continued)

OTHER PUBLICATIONS

Kalies et al. "Immobilization of gold nanoparticles on cell culture surfaces for safe and enhanced gold nanoparticle-mediated laser transfection." Journal of Biomedical Optics, Jul. 2014 • vol. 19(7), pp. 070505-1-070505-3. (Year: 2014).*

(Continued)

*Primary Examiner* — William H. Beisner
(74) *Attorney, Agent, or Firm* — Vorys, Sater, Seymour and Pease LLP

(57) ABSTRACT

The invention relates to a method to increase the permeability of the plasma membrane of cells by introducing at least one cell on or near a structure comprising particles able to absorb electromagnetic radiation. The particles, present in a concentration ranging between 0.001 vol % and 20 vol %, are embedded in the material of the structure. At least 60% of the particles present in the structure are embedded in the material in such a way that the shortest distance L between these particles and the free area surface S of the structure ranges between 1 nm and 500 nm.

The invention further relates to a structure suitable for use in a photothermal process to permeabilize cells and to the use of such structure.

11 Claims, 19 Drawing Sheets

(56) References Cited

U.S. PATENT DOCUMENTS

2007/0292678 A1* 12/2007 Hikmet ................ B82Y 10/00
2010/0231433 A1* 9/2010 Tishin ................ H05K 9/0075
                                                              264/45.3

FOREIGN PATENT DOCUMENTS

WO    2016/050357 A1    4/2016
WO    2021/057430 A1    4/2021

OTHER PUBLICATIONS

Lyu et al. "A Universal Platform for Macromolecular Delivery into Cells Using Gold Nanoparticle Layers via the Photoporation Effect." Adv. Funct. Mater. 2016, 26, 5787-5795 (Year: 2016).*
ISR/WO dated Dec. 22, 2020 for parent application PCT/EP2020/076287.

* cited by examiner

METHOD TO INCREASE THE PERMEABILITY OF THE PLASMA MEMBRANE OF CELLS AND A STRUCTURE SUITABLE FOR USE IN SUCH METHOD

FIELD OF THE INVENTION

The present invention relates to a method to increase the permeability of the plasma membrane of cells by introducing cells on or near a structure comprising embedded particles and by irradiating this structure. The method according to the present invention does not require contact between the particles and the cells. The invention further relates to a structure suitable in a method to increase the permeability of the plasma membrane of cells.

BACKGROUND ART

Intracellular delivery of exogenous compounds in cells is a common requirement in many biotechnological and biomedical applications. Examples are the creation of mutant cell lines for fundamental research, drug screening of biopharmaceutical compounds and the production of cells (e.g. CAR-T cells) for cell-based immunotherapy. Regardless of the specific application, the common challenge is to overcome the cell membrane, which represents a major obstacle in particular for large macromolecules like DNA, RNA or proteins. In recent years, the field has seen a marked increase in research on new physical transfection methods that should be as efficient as possible in delivering molecules, in particular large macromolecules, with as little cytotoxicity as possible.

Physical methods for the delivery of compounds into cells have attracted considerable interest. Such methods have in common that the permeability of the cell membrane is increased, allowing passage of compounds across the cell membrane.

Nanoparticle (NPs) sensitized photoporation is a promising upcoming physical method to deliver compounds into cells. In photoporation, the cell membrane is temporarily permeabilized by a combination of laser irradiation and light-responsive nanoparticles. Cells are first incubated with the nanoparticles, typically gold particles, iron oxide particles or carbon particles, which can adsorb to the cell membrane. Next, laser irradiation is applied so that the cell membrane becomes permeabilized through photothermal or photochemical effects, such as local heating, induction of pressure waves or the generation of reactive oxygen species.

Although photoporation is a promising technique for example to produce engineered cells for cell therapy, there is a generic safety concern about bringing nanoparticles in contact with cells. Indeed, there is quite some uncertainty about potential toxicological effects of nanoparticles in general. Additionally, plasmonic nanoparticles, such as gold nanoparticles, tend to fragment into smaller pieces upon intense laser illumination used in photoporation. Reportedly, nanometer sized gold particles have the potential to be genotoxic when internalized into cells. Considering that the photoporation method requires close contact between the plasmonic nanoparticles and the cells, there might be a nanotoxicological concern to use photoporation for example for transfecting cells to be used in cell therapies.

Therefore, it is of current interest to develop methods avoiding the direct contact of the plasmonic nanoparticles with the cells during photoporation.

U.S. Pat. No. 9,957,476 describes a system for the poration of cells by using plasmonic nanoparticles. The system uses a laser to create an optical trap to position a nanoparticle near the cell and uses a laser directed on the optically trapped particle for causing laser-induced breakdown of the optically trapped particle thus causing poration of the cell. The system has however a limited throughput and does not allow upscaling for the treatment of a significant number of cells. Consequently, the system is not suitable for the production of a substantial number of engineered cells for cell therapy.

U.S. Pat. No. 9,139,416 describes a microfluidic device comprising a substrate having a microchannel whereby the walls of the microchannel are provided with nanowires. Upon irradiation with laser light cells while flowing through the channel can be photoporated. The device does however not allow to tune the distance between the plasmonic structure and the cells as would be needed to maximize the performance of the system, especially when dealing with different cell types. Furthermore, the device suffers from damage of the nanowires and thus has a limited useful lifetime.

EP2272945 describes a method to porate cells by placing a cell at or near a surface of a substrate provided with surface structures coated with a thin metal layer such as a gold layer and by irradiating the surface of the substrate with a laser pulse. Such method has the disadvantage that the cell membrane is permeabilized at one side, i.e. the side where the cells are in contact with the surface structures of the substrate (the bottom side of the cells), while the compounds that need to be delivered into the cells are present primarily at the opposite side (the upper side of the cells). This restricts the efficiency by which molecules can enter cells, especially the efficiency by which large molecules can enter cells.

SUMMARY OF THE INVENTION

It is an object of the present invention to provide a method to increase the permeability of the plasma membrane of cells thereby avoiding the drawbacks of the methods known in the art.

It is another object of the present invention to provide a method to increase the permeability of cells by a photothermal process, in particular by radiation with electromagnetic radiation as for example laser radiation.

It is another object of the present invention to provide a method to increase the permeability of the plasma membrane of cells by using a structure comprising particles embedded in the structure, by introducing cells on or near this structure and by irradiating this structure with electromagnetic radiation.

It is a further object of the present invention to provide a method to increase the permeability of cells whereby direct exposure of the cells to the particles, for example nanoparticles or their constituents is limited or even avoided.

It is a further object of the present invention to provide a method to increase the permeability of cells by using pulsed laser radiation, for example nanosecond pulsed radiation.

Additionally, it is an object to provide a method to increase the permeability of cells having an enhanced efficiency for the intracellular delivery of cell-impermeable substances in particular for the intracellular delivery of macromolecules.

It is also an object to provide a structure comprising particles able to absorb electromagnetic radiation, such as nanoparticles, to increase the permeability of the plasma membrane of cells whereby the particles and their constituents are mostly, and preferably entirely, retained within the structure upon laser activation.

Furthermore, it is an object to provide a method to increase the permeability of cells suitable for use in drug screening, in cell therapy, in immunotherapy, in gene therapy in cell labelling and in the production of engineered cells.

It is an object of the present invention to provide a structure suitable for use in a photothermal process to permeabilize cells that are introduced on or near that structure.

It is a further object of the present invention to provide a structure that can be activated multiple times by laser irradiation so as to repeatedly increase the permeability of cells.

According to a first aspect of the present invention a method to increase the permeability of the plasma membrane of cells is provided. The method comprises the steps of providing a structure comprising a material and comprising particles able to absorb electromagnetic radiation. The particles have an average equivalent spherical diameter d and are embedded in the material. The structure defines a volume V and a free area surface S. The particles are present in the structure in a concentration ranging between 0.001 vol % and 20 vol % (volume particles/volume structure). At least P percent of the particles present in the structure are embedded in the material in such a way that the closest distance L between this P percent of particles and said free area surface S of the structure ranges between 1 nm and 500 nm, with P being at least 60 percent;

introducing at least one cell on or near said structure, preferably at a distance of less than 100 μm from said structure;

irradiating said structure with electromagnetic radiation.

Upon irradiation of the structure with electromagnetic radiation, the particles present in the structure, i.e. embedded in the structure, cause a photothermal effect causing the structure and the free area surface S of the structure to become locally and temporarily heated. The photothermal effect causes in particular a local and temporary heating of the material close to an irradiated particle. Consequently, the temperature at the free area surface close to a particle will increase. The local and temporary heating induced upon irradiation may result in the permeabilization or perforation of a membrane or barrier, for example the plasma membrane of cells, that is in contact with or close to the structure.

The temperature at the free area surface S closest to a particle reaches for example a temperature of at least 10° C. above its initial temperature, for example a temperature of at least 20° C. or at least 30° C. above its initial temperature, and this for at least 1 ns over an area of at least 1 nm². It is clear that the temperature increase at the free area surface S closest to a particles may be higher, for example at least 50° C. or at least 100° C. above its initial temperature for at least 1 ns over an area of at least 1 nm².

The temperature at the free area surface S closest to the particles reaches for example a temperature of 60° C., which is the temperature at which cell membranes are considered to become permeable. Consequently, cells that are in contact with or close to the locally heated area of the structure, i.e. in contact or close to the free area surface closest to the irradiated particles will become permeable. It is clear that the temperature at the free area surface S closest to a particles may be higher than 60° C. and may reach for example a temperature above 100° C.

The method according to the present invention allows to increase the permeability of cells introduced on or near the structure without requiring direct contact between the particles and the cells. Introducing the cells on the structure means that the cells are introduced in such a way that the cells or at least part of the cells contact the structure, i.e. the free area surface S of the structure. Introducing the cells near the structure means that the cells or at least part of the cells are introduced in such a way that they reach the structure at a distance of 100 μm or less than 100 μm, for example at a distance of 50 μm, 20 μm, 10 μm, 5 μm, 3 μm, 2 μm, 1 μm, 0.5 μm or 0.1 μm. This means that the (closest) distance between the cells or at least part of the cells and the free area surface S of the structure is 100 μm or lower for example 50 μm, 20 μm, 10 μm, 5 μm, 3 μm, 2 μm, 1 μm, 0.5 μm or 0.1 μm.

Furthermore the method according to the present invention has the advantage that no material or substantially no material of the particles present in the structure is released. With substantially no material is meant that less than 1%, preferably less than 0.5%, less than 0.1%, less than 0.05% of the total particle mass of the particles present in the structure is released.

For the purpose of this invention, the term 'volume' of a structure (V), also referred to as inner volume of a structure, is defined as the total space occupied by this structure, i.e. the total space occupied by the material and the particles of the structure.

The term 'free area surface' of a structure (S) is defined as the total outer surface of the structure enclosing the (inner) volume of the structure, i.e. the total surface of the structure that is in direct contact with the environment. In case the structure is submerged in a fluid, for example a liquid (such as a medium comprising (biological) cells or a gas for example air), and the structure comprises a material that is impermeable for that fluid, the free area surface of the structure can also be defined as the total surface of the material of the structure that is or may have contact with that fluid.

Preferably, the ratio of the free area surface S of a structure to the volume of the structure, i.e. the ratio S/V, ranges between $10^{-2}$ and $10^2$ $\mu m^{-1}$, for example between $10^{-1}$ and 50 $\mu m^{-1}$ or between 1 and 10 $\mu m^{-1}$.

The shortest distance L of a particle to the free area surface S of the structure is defined as the shortest distance measured from the outer surface of a particle to the free area surface S of the structure.

The average equivalent spherical diameter d of a particle (for example a spherical particle, a longitudinal particle or an irregularly shaped particle) is defined as the average diameter of a sphere of equivalent volume as that particle. The average equivalent spherical diameter d of a particle can also be referred to as the average equivalent volume diameter of a particle. In case the particle comprises a spherical particle, it is clear that the average equivalent spherical diameter corresponds with the average diameter of that particle.

As mentioned above the concentration of particles able to absorb electromagnetic radiation present in the structure according to the present invention ranges between 0.001 vol % and 20 vol %. More preferably, the concentration of particles able to absorb electromagnetic radiation present in the structure according to the present invention ranges between 0.01 vol % and 10 vol % or between 0.01 vol % and 5 vol % and is for example 0.05 vol %, 0.1 vol %, 0.2 vol %, 0.5 vol %, 1 vol %, 2 vol % or 5 vol %.

The particles present in the structure according to the present invention are preferably embedded in the material in such a way that the shortest distance L of at least 60% of the particles present in the structure and the free area surface S ranges between 1 nm and 500 nm, for example between 2 nm and 500 nm or between 5 nm and 500 nm. More preferably, the particles are embedded in the material in such a way that the shortest distance L of at least 70%, at least 80% or at least 90% of the particles present in the structure and the free area surface S ranges between 1 nm and 500 nm, for example between 2 nm and 500 nm or between 5 nm and 500 nm.

In preferred embodiments the particles are embedded in the material in such a way that the shortest distance L of at least 60% of the particles present in the structure and the free area surface S ranges between 1 nm and 250 nm, for example between 2 nm and 250 nm or between 5 nm and 250 nm. More preferably, the particles are embedded in the material in such a way that the shortest distance L of at least 70% of the particles present in the structure, at least 80% of the particles present in the structure, at least 90% of the particles and the free area surface S of the structure ranges between 1 nm and 250 nm, for example between 2 nm and 250 nm or between 5 nm and 250 nm.

In other embodiments the particles are embedded in the material in such a way that the shortest distance L of at least 60% of the particles present in the structure and the free area surface S ranges between 1 nm and 100 nm, for example between 2 nm and 100 nm or between 5 nm and 100 nm. More preferably, the particles are embedded in the material in such a way that the shortest distance L of at least 70% of the particles present in the structure, at least 80% of the particles present in the structure, at least 90% of the particles and the free area surface S of the structure ranges between 1 nm and 100 nm, for example between 2 nm and 100 nm or between 5 nm and 100 nm.

Preferably, the surface density of the particles positioned at a shortest distance L from the free area surface S of the structure with L ranging between 1 nm and 500 nm ranges between $10^{-4}$ $\mu m^{-2}$ and $1/d^2$ (with d the average equivalent spherical diameter of the particles expressed in $\mu m$), for example between $2\times10^{-4}$ $\mu m^{-2}$ and $2$ $\mu m^{-2}$ or between $2\times10^{-3}$ $\mu m^{-2}$ and $0.2$ $\mu m^{-2}$. The surface density of particles is thereby defined as the number of particles N present in said structure multiplied with the percent P of the particles positioned at a shortest distance L from the free area surface S (with L ranging between 1 nm and 500 nm, for example between 5 nm and 500 nm) divided by the free area surface of the structure. The surface density of the particles positioned at a distance L ranging between 1 nm and 500 nm, for example between 5 nm and 500 nm, can be calculated using the formula N·P/S.

In preferred embodiments the surface density of the particles positioned at a shortest distance L from the free area surface S of the structure with L ranging between 1 nm and 250 nm ranges between $10^{-4}$ $\mu m^{-2}$ and $1/d^2$, for example ranging between $2\times10^{-4}$ $\mu m^{-2}$ and $2$ $\mu m^{-2}$ or between $2\times10^{-3}$ $\mu m^{-2}$ and $0.2$ $\mu m^{-2}$.

In other preferred embodiments the surface density of the particles positioned at a shortest distance L from the free area surface S of the structure with L ranging between 1 nm and 100 nm ranges between $10^{-4}$ $\mu m^{-2}$ and $1/d^2$, for example ranging between $2\times10^{-4}$ $\mu m^{-2}$ and $2$ $\mu m^{-2}$ or between $2\times10^{-3}$ $\mu m^{-2}$ and $0.2$ $\mu m^{-2}$.

The surface density of iron oxide particles having an average equivalent spherical diameter of 160 $\mu m$ ranges for example between $2\times10^{-4}$ $\mu m^{-2}$ and $2$ $\mu m^{-2}$, between $1\times10^{-3}$ $\mu m^{-2}$ and $0.4$ $\mu m^{-2}$ or between $2\times10^{-3}$ $\mu m^{-2}$ and $0.2$ $\mu m^{-2}$.

In preferred embodiments of a structure according to the present invention all or substantially all particles are completely embedded in the material of the structure. This means that all or substantially all particles of a structure are completely surrounded by the material of the structure. Consequently, no particles or substantially no particles are exposed to the free area surface of the structure.

For the purpose of this invention the term 'particles that are exposed to the free area surface' refers to all particles having at least part of their outer surface emerging from the free area surface of the structure and being in contact with the outside environment around the structure.

For the purpose of this invention 'substantially all particles' means at least 95% of the particles, preferably at least 99% of the particles, for example at least 99.9% of the particles.

Similarly, for the purpose of this invention 'substantially no particles' means less than 5% of the particles, preferably less than 1% of the particles, for example less than 0.1% of the particles.

The particles that are embedded in a structure according to the present invention, may comprise any particle able to absorb electromagnetic radiation and adapted to generate a photothermal effect upon irradiation with electromagnetic radiation.

The particles may comprise microparticles, nanoparticles or a combination of microparticles and nanoparticles.

The term 'microparticle' refers to particles having an equivalent spherical diameter ranging between 1 $\mu m$ and 100 $\mu m$. The term 'nanoparticle' refers to particles having an equivalent spherical diameter ranging between 1 nm and 1000 nm.

The particles may have any shape. They may for example be spherical, elliptical, rod-like shaped, pyramidal, branched, or may have an irregular shape.

The particles may be solid particles, may have a shell structure or a core-shell structure comprising one or more materials.

Preferred particles comprise metal particles, metal oxide particles, carbon or carbon based particles, particles comprising one or more light absorbing compounds or particles loaded or functionalized with one or more light absorbing compounds.

Examples of metal particles comprise gold particles, silver particles, platinum particles, palladium particles, copper particles and alloys thereof. Preferred metal particles comprise gold particles, silver particles and alloys thereof.

Examples of metal oxide particles comprise iron oxide, titanium oxide, zirconium oxide, cerium oxide, zinc oxide and magnesium oxide.

Examples of carbon or carbon based particles comprise graphene quantum dots, (reduced) graphene oxide and carbon nanotubes.

Examples of particles comprising one or more light absorbing compounds or particles loaded or functionalized with one or more light absorbing compounds comprise particles comprising, loaded or functionalized with synthetic organic or inorganic absorbers as well as particles comprising, loaded or functionalized with naturally occurring absorbers or derivatives thereof. Particular examples comprise liposomes, solid lipid nanoparticles, polymer based particles comprising loaded or functionalized with light absorbing dye molecules such as indocyanine green, inorganic quantum dots (having low fluorescence quantum yield), naturally occurring light absorbers like pigments (such as melanin, rhodopsin, photopsins or iodopsin) and synthetic analogs like polydopamine, or photosensitizers used in photodynamic therapy.

The particles preferably comprise biocompatible particles. More preferably, the particles comprise clinically approved particles or are composed of clinically approved particles.

The particles may comprise individual particles or a combination or cluster of two or more particles positioned close to each other.

A structure according to the present invention may comprise one type of particles or a combination of different particles, for example particles having a different size, a different composition and/or a different shape.

The dimensions of a particle, for example a width, height or diameter of a particle, can be determined using Transmission Electron Microscopy (TEM), Scanning Electron Microscopy (SEM) or atomic force microscopy (AFM).

The size of the particles is preferably defined by the equivalent spherical diameter d (also referred to as the equivalent volume diameter).

The material of the structure into which the particles able to absorb electromagnetic radiation are embedded comprises for example an inorganic material or an inorganic based material, for example silica or a silica based material or a ceramic or ceramic based material, an organic material or organic based material, such as a carbon or carbon based material or a polymer or polymer based material. The material of the structure may also comprise a composite material comprising at least one of the above mentioned materials, for example a composite material comprising an organic and an inorganic material.

Preferred materials of the structure comprise or are based on polystyrene, polycaprolacton, ethylcellulose, cellulose acetophthalate, polylactic acid, polylactic-co-glycolic acid, cellulose, polyvinylalcohol, polyethylene glycol, gelatin, collagen, silk, alginate, hyaluronic acid, dextran, starch, polycarbonate or polyacrylate.

In preferred embodiments the structure comprises a surface modified material, for example a surface modified polymer material. The surface modification comprises for example the application of a coating (for example collagen) to enhance cell attachment to the material of the structure.

The structure may comprise a continuous or discontinuous structure.

The structure may comprise a porous or non porous structure. Porous structures can be preferred as they have the advantage to have a high free area surface and thus have a large surface available to be exposed to cells that are introduced on or near the structure according to the method of the present invention. Preferably, the porous structure has a pore size that allows partial or complete penetration of the cells introduced on or near the structure into the pores. Preferably, the porous structure has a pore size that does not restrict access of molecules present in the cell medium to the cells.

The porosity of a structure is defined as the ratio of the volume of the pores or voids of a structure over the total volume occupied by that structure, i.e. the sum of the volume V of the structure (the volume of the material and the particles embedded in the material) and the volume of the pores or voids of that structure. The porosity may range between 0% and 100%. In case the structure comprises a porous structure the porosity of the structure is preferably at least 50%, at least 60% at least 80%, at least 90%, at least 95% or at least 99%.

The structure may be flat or planar or the structure may be non-flat, for example tubular. A structure The surface of the structure that is irradiated with electromagnetic radiation can be flat or non-flat.

The structure may have a smooth or non-smooth surface. A non-smooth surface comprises for example a surface provided with protrusions.

The structure has preferably a thickness ranging between 0.1 µm and 1000 µm, for example between 0.1 µm and 100 µm or between 1 µm and 10 µm.

The thickness of the structure is defined as the distance through the material of the structure along its shortest dimension. For instance, for a flat or planar structure, the thickness corresponds with the distance of the structure measured along the direction perpendicular to the horizontal plane. For a long tubular structure, the thickness corresponds with the radial diameter of the tubular structure.

A first group of embodiments comprises non-porous structures comprising a material and particles able to absorb electromagnetic radiation embedded in the material. Examples comprise a polymer sheet or polymer foil comprising particles able to absorb electromagnetic radiation embedded in the polymer sheet or polymer foil.

A particular preferred embodiment comprises a polymer sheet comprising or based on polystyrene, polycaprolacton, ethylcellulose, cellulose acetophthalate, polylactic, polylactic-co-glycolic acid, cellulose, polyvinylalcohol, polyethylene glycol, gelatin, collagen, silk, alginate, hyaluronic acid, dextran, starch, polycarbonate or polyacrylate.

The polymer sheet comprises for example iron oxide particles and/or carbon particles embedded in the polymer sheet.

The structures of this first group have for example a thickness t, a length A and a width A'. The thickness t ranges preferably between 0.1 µm and 100 µm, for example between 0.1 µm and 10 µm.

The volume V of the structure corresponds with t.A.A'.

As the length and width of a structure of the first group is typically substantially larger than the thickness t of the structure the free area surface of a structure of the first group can be estimated as being equal to 2.A.A'. The free area surface of the structure that is irradiated corresponds with one of the surfaces of the structure (for example the top surface or the bottom surface) and can thus be estimated as being equal to A.A'.

Consequently, the ratio of the free area surface S of the structure over the volume V of the structure, i.e. S/V, corresponds to 1/t.

A second group of embodiments, comprises porous structures comprising a material and particles able to absorb electromagnetic radiation embedded in the material. Examples comprise a porous polymer structure with the particles embedded in the porous polymer structure.

Examples of porous structures comprise structures comprising fibres (for example polymer fibres), structures comprising particulates (for example polymer particulates), structures comprising a combination of fibres and particulates (for example a combination of polymer fibres and/or polymer particulates) and structures comprising foam (for example polymer foam). The fibres and/or particulates can be interconnected or not. The particulates as for example the polymer particulates may comprises spherical particulates as well as irregular shaped particulates. The particles able to absorb electromagnetic radiation are preferably embedded in the fibres, the particulates, or the foam, preferably in such a way that the particles are not (partially) exposed to the free area surface of the structure.

A first example of a structure of the second group is a structure comprising (polymer) fibres. The (polymer) fibres have for example a fibre diameter ranging between 0.1 µm and 10 µm, for example a diameter of 0.5 µm or 1 µm. The (polymer) fibres can be interconnected or not. The (polymer) fibres can be obtained by any technique known in the art. A preferred technique to manufacture the (polymer) fibres is electrospinning. Alternative techniques comprise wet spinning, melt spinning, extrusion spinning, dry spray wet spinning, emulsion spinning and suspension spinning. Preferred examples of polymer comprise polystyrene fibres, polycaprolacton fibres, ethylcellulose fibres, cellulose acetophthalate fibres, polylactic acid fibres and polylactic-co-glycolic acid based fibres. The (polymer) fibres can be surface modified.

As the (polymer) fibres can be considered as long cylinders with a diameter corresponding to the fibre diameter $d_{fibre}$ and a length corresponding to the length of the fibre $L_{fibre}$, the volume of the fibre $V_{fibre}$ corresponds with and $$\pi\left(\frac{d_{fibre}}{2}\right)^2 L_{fibre}$$

the free area surface of the fibre $S_{fibre}$ corresponds with $\pi d_{fibre} L_{fibre}$. Consequently, the ratio of the free are surface $S_{fibre}$ to the volume $V_{fibre}$ corresponds with $4/d_{fibre}$.

A second example of a structure of the second group is a structure particulates as for example polymer (micro) spheres. The particulates have for example a particulate diameter ranging between 0.1 µm and 10 µm, for example a diameter of 0.5 µm or 1 µm. The polymer particulates can be interconnected or not. The (polymer) particulates can be obtained by any technique known in the art. Preferred examples of particulates comprise polystyrene, polycaprolacton, ethylcellulose, cellulose acetophthalate, polylactic acid, polylactic-co-glycolic acid based fibres. The polymer particulates can be surface modified.

In case the particulates are microspheres with a diameter $d_{ms}$, the volume of the microspheres $V_{ms}$ corresponds to $$\frac{4}{3}\pi\left(\frac{d_{ms}}{2}\right)^3$$

and the free area surface of the microspheres $S_{ms}$ corresponds to $$4\pi\left(\frac{d_{ms}}{2}\right)^2.$$

Consequently, the ratio of the free area surface $S_{ms}$ over the volume of the microspheres $V_{ms}$ is $6/d_{ms}$.

The cells are for example introduced on or near the structure by applying a suspension comprising cells on or near the structure. The cells can either be introduced continuously on or near the structure or discontinuously on or near the structure.

Concentration of the cells in the suspension ranges preferably between 1 and $10^6$ cells per mL.

In preferred methods the suspension, i.e. the cells are cultured on or near the structure during a certain time period.

In alternative methods the cells are treated by activation of the structure with electromagnetic irradiation immediately or shortly after their introduction on or near the structure.

The structure and in particular the particles embedded in the structure is/are preferably irradiated by a pulsed radiation source, although irradiation by a continuous wave radiation source can also be considered. The structure can be irradiated by one or more pulses.

When a pulsed radiation source is used, the pulses preferably have a duration in the range of 1 fs and 1 ms, for example in the range of 1 fs and 100 µs, in the range of 10 fs and 10 µs, in the range of 10 fs and 1 µs or in the range of 10 fs and 10 ns.

The fluence (electromagnetic energy delivered per unit area) per pulse of the radiation source ranges preferably between 0.001 and 1000 J/cm², for example between 0.001 and 100 J/cm², between 0.01 and 10 J/cm², for example 0.1 J/cm² and 1 J/cm².

The wavelength of the radiation source may range from the ultraviolet region to the infrared region. In preferred methods, the wavelength range of the radiation used is in the visible to the near infrared region.

The method according to the present invention shows an enhanced efficiency, for example an enhanced transfection efficiency, compared to methods known in the art as for example the method described in EP2272945. Although Applicant does not want to be bound by any theory, the Applicant is of the opinion that the enhanced efficiency is a direct result of the increased contact of the cells and the structure. Because of the increased contact between the cells and the structure, a larger area of the cell membrane will be permeabilized with the consequence that more and/or larger molecules can enter the cells. In case the structure comprises a porous structure, the efficiency can be further increased as the free area surface is larger and the cells can reach the free area surface of the structure from different sides.

Until now it was believed that delivering large macromolecules into cells requires high intensity laser pulses so as to create vapour nanobubbles and to cause local pressure waves that may permeabilize a membrane of a cell, for example the plasma membrane of a cell. Surprisingly, it was found that the method according to the present invention allows to permeabilize a membrane of a cell, for example the plasma membrane of a cell, using a much lower intensity single laser pulse, for example a single laser pulse having a fluence ranging between 0.001 J/cm² and 1 J/cm², preferably ranging between 0.01 J/cm² and 0.5 J/cm², more preferably between 0.05 J/cm² and 0.2 J/cm². Furthermore the method according to the present invention allows to induce relatively large pores even when using low laser intensities and does allow intracellular delivery of relatively large macromolecules, for example macromolecules having a nominal size of 500 kDa.

A further advantage of the method according to the present invention is that fragmentation or release of the particles embedded in the structure is avoided. ICP-MS analysis demonstrated that no detectable amounts of the material of the particles are released. On the one hand this means that cells are not exposed to potentially toxic material of the particles, while on the other hand it means that the particles remain intact and functional after irradiation. In photoporation techniques known in the art, the irradiated (nano)particle often becomes fragmented upon a single laser pulse. Consequently, in techniques known in the art, (nano) particles can often be used only once. In the method according to the present invention, the structure can be used for repeated irradiation.

A further advantage of the method according to the present invention is the ease of fabrication of the structure.

According to a second aspect of the present invention, a structure suitable for use in a photothermal process to permeabilize cells, in particular the plasma membrane of cells, that are introduced on or near said structure is provided. The structure comprises a material and particles able to absorb electromagnetic radiation embedded in the material. The particles have an average equivalent spherical diameter d. The structure defines a volume V and a free area surface S. The particles are present in the structure in a concentration ranging between 0.001 vol % and 20 vol % (volume particles/volume structure), for example ranging between 0.01 vol % and 10 vol % or between 0.01 vol % and 10 vol %. At least P percent of the particles present in the structure are positioned at a shortest distance L from the free area surface of the structure with L ranging between 1 nm and 500 nm, whereby P is at least 60.

The structure may comprise any type of structure described above.

The structure according to the present invention is in particular suitable for use in drug screening, in cell therapy, in immunotherapy, in gene therapy, in cell labelling and in the production of engineered cells.

The structure is in particular suitable for use in intracellular delivery of nucleic acids, including oligonucleotides, siRNA, mRNA or pDNA.

The structure is also suitable for use in the intracellular delivery of nucleoproteins, including ribonucleoproteins, such as Cas9/gRNA.

Furthermore, the structure is suitable for use in the intracellular delivery of peptides and proteins, such as nanobodies or antibodies.

In addition, the structure is suitable for use in the intracellular delivery of contrast agents such as fluorescently labeled polymers, quantum dots, iron oxide nanoparticles and gadolinium chelates.

The structure is furthermore suitable for use in the intracellular delivery of plasmonic nanoparticles for example for sensing and characterization purposes as for example LSPR sensors (localized surface plasmon resonance) or for SERS (surface enhanced raman spectroscopy).

The structure according to the present invention is suitable for use in in vitro and ex vivo applications. The structure is furthermore suitable for use in in vivo applications.

According to a third aspect of the present invention, the use of the structure according to the present invention in particular in in drug screening, in cell therapy, in immunotherapy, in gene therapy, in cell labelling, in the production of engineered cells and in protein interference studies is provided. The structure can be used in in vitro and ex vivo applications. The structure can furthermore be used in in in vivo applications.

In a preferred use the structure is used in a method to increase the permeability of cells as described above.

BRIEF DESCRIPTION OF THE DRAWINGS

The present invention will be discussed in more detail below, with reference to the attached drawings, in which.

DESCRIPTION OF EMBODIMENTS

Figure 1:
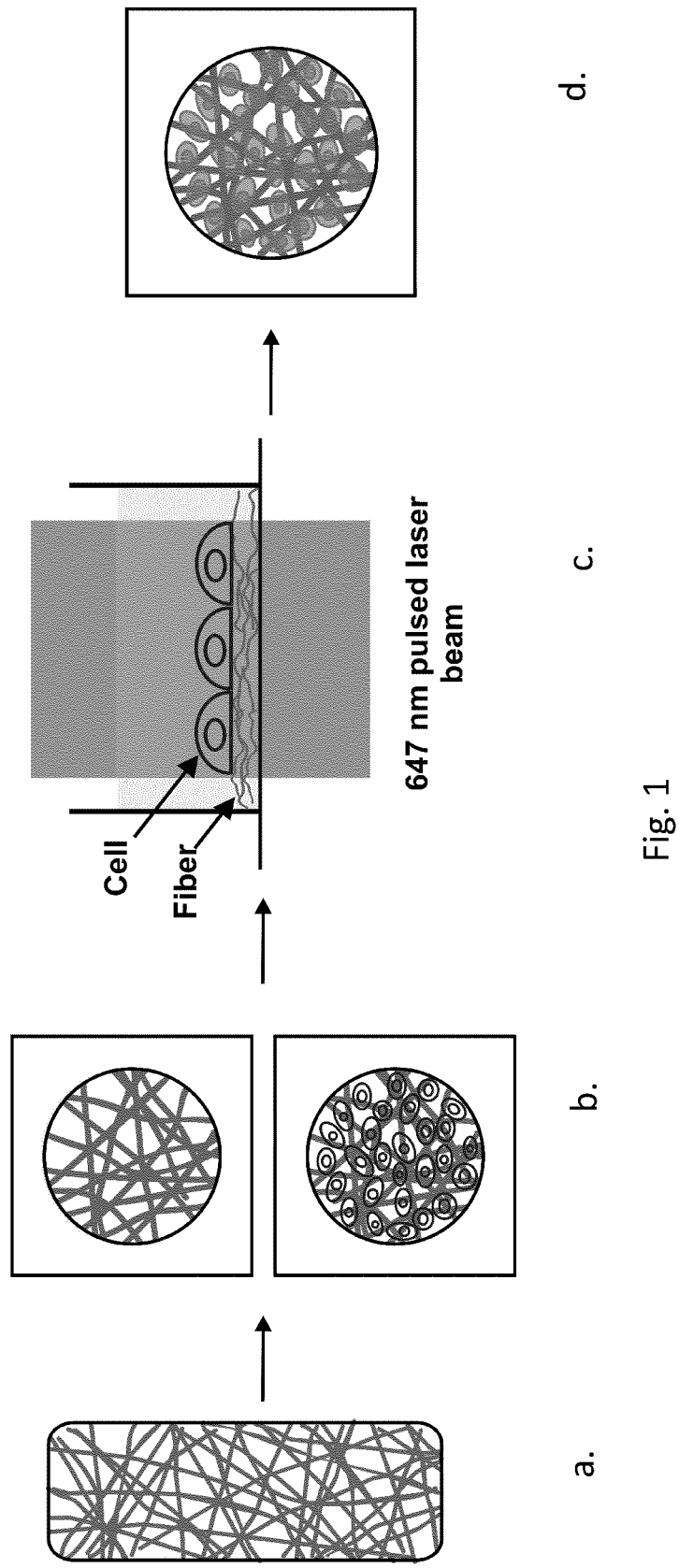
FIG. 1 schematically illustrates the method to increase the permeability of a cell membrane according to the present invention.

The present invention will be described with respect to particular embodiments and with reference to certain drawings, but the invention is not limited thereto but only by the claims. The drawings are only schematic and are non-limiting. The size of some of the elements in the drawings may be exaggerated and not drawn to scale for illustrative purposes. The dimensions and relative dimensions do not correspond to actual reductions to practice the invention.

When referring to the endpoints of a range, the endpoints values of the range are included.

When describing the invention, the terms used are construed in accordance with the following definitions, unless indicated otherwise.

The terms 'first', 'second' and the like used in the description as well as in the claims, are used to distinguish between similar elements and not necessarily describe a sequence, either temporally, spatially, in ranking or in any other manner. It is to be understood that the terms so used are interchangeable under appropriate circumstances and that the embodiments of the invention described herein are capable of operation in other sequences than described or illustrated herein.

The term 'and/or' when listing two or more items, means that any one of the listed items can by employed by itself or that any combination of two or more of the listed items can be employed.

The term 'cell' refers to all types of biological cells, including eukaryotic cells an prokaryotic cells.

The terms 'increase the permeability of', 'permeabilize', 'permeabilizing' and 'permeabilization' refer to any way to alter the permeability of a membrane or barrier, for example the plasma membrane of a cell, at least partially or locally. After permeabilization, the membrane or barrier, for example the plasma membrane of a cell is altered in such a way that it is more permeable for one or more types of compounds as for example molecules, macromolecules, particles or nanoparticles.

The terms 'perforate', 'perforating' or 'perforation' refer to any way to provide a membrane or barrier, for example the plasma membrane of a cell, with one or more openings, holes or pores. By perforating a membrane or barrier, for example the plasma membrane of a cell, openings are created into the membrane or barrier, for example the plasma membrane of a cell, allowing the transport of compounds, such as molecules, macromolecules, particles or nanoparticles across the membrane or barrier, for example across the plasma membrane of a cell.

For the purpose of this invention the terms 'increase the permeability of', 'permeabilize', 'permeabilizing' and 'permeabilization' and the terms 'perforate', 'perforating' and 'perforation' are interchangeably used.

Similarly, for the purpose of this invention the terms 'opening', 'hole', and 'pore' are interchangeably used.

Example 1 Porous Structure Comprising a Web of Nanofibres and Particles Embedded in the Nanofibres A second embodiment of a structure according to the present invention comprises a porous structure comprising nanofibres and particles able to absorb electromagnetic radiation embedded in the nanofibres. The below described examples comprise polycaprolactone as material of the structure and iron oxide nanopowder as particles able to absorb electromagnetic radiation. It is clear that other materials and other particles can be considered as well.

1.a Synthesis and Characterization of Photothermal Electrospun Nanofibres

The following materials are used for the synthesis of the web of nanofibres:

Polycaprolactone (PCL, Mw≈70,000 g/mol);
N,N-Dimethylformamide (DMF);
Tetrahydrofuran (THF);
iron oxide ($Fe_3O_4$) nanopowder (IONP) (#MKBW3262, Sigma-Aldrich, Belgium);
Poly(allylamine hydrochloride) (PAH, Mw=17,560 g/mol, #MKBZ2824V, Sigma-Aldrich, Belgium);
concentrated sulfuric acid solution (96%) (Sigma-Aldrich);
Collagen I Rat Protein (Thermo Fisher Scientific, #A1048301, Gibco™, Belgium).

IONP was re-dispersed in a 1:1 DMF/THF solution to which PCL in different concentrations between 0 vol % and 1.15 vol % was added.

The thus obtained mixture was used to manufacture nanofibres by electrospinning. The nanofibres were collected on microscope glass slides (#1000912, Marienfeld, Germany) mounted on a grounded rotating collector.

During electrospinning, unless otherwise specified, the applied voltage, flow rate and electrospinning distance were fixed at 10 kV, 0.3 ml/h and 20 cm, respectively. The grounded rotating collector was set at a rotating speed of 500 rpm. After 30 minutes (or specifically indicated time) the electrospinning process was stopped and glass slides with the nanofibre web were separated from the rotating collector and sterilized by UV irradiation for 45 minutes in a laminar flow cabinet.

The size and diameter of the nanofibres was determined using scanning and electron microscopy. The average diameter of fibres without IONP was 300 nm. The average diameter did not significantly changed when including IONP up to 1.15 vol %.

The thickness of the structure was investigated using confocal microscopy. With increasing electrospinning duration, the structure became gradually thicker up to 4 μm after 1 hour. As the webs did not change much after 30 minutes, an electrospinning time of 30 minutes was chosen.

When using increasing amounts of IONP to the nanofibres, the thickness of the nanofibre web did not change significantly. This clearly indicates that the thickness of the nanofibre web is independent of the IONP content within the used range.

IONP was embedded in the nanofibres. This could be clearly seen by SEM using a voltage of 20 kV. SEM images revealed that IONP could be present as individual particles or as clusters of two or more individual particles. For simplicity, embedded IONP is referred to as 'IONP clusters' or 'clusters' with the understanding that the terms 'IONP clusters' or clusters include both individual particles and clustered particles. SEM allowed to quantify the apparent density of IONP clusters throughout the web per 1000 $\mu m^2$ of area in the SEM images. The density linearly increased from 1.7 to 192 clusters/1000 $\mu m^2$ as the IONP content was increased from 0.0046 vol % to 1.15 vol %.

1.b Preparation of a Nanofibre Web as Cell Culture Substrate 8-well Secure-Seal™ double sided adhesive spacers (#S24737, Invitrogen) were sterilized by UV irradiation for 45 minutes in a laminar flow cabinet. After removing the protective sealing from one side of the adhesive spacers, they were gently stuck on the nanofibre web. Next, these samples were immersed in distilled water for 3 minutes for easy removal of the web (with adhesive spacers on top) from the glass slides. The web was manually cut into smaller pieces with either one or 4 adhesive wells per piece (into which cells can be grown) and stored in PBS buffer.

Next, these cell culture substrates were further modified with collagen for optimal cell attachment. Cell culture substrates were immersed in 32% sulfuric acid solution (3 ml per well of 6-well plate) for 3 minutes. After washing with distilled water, they were immersed into an aqueous solution of the polyelectrolyte PAH (2 mg/ml, 0.5M NaCl) for 15 minutes and rinsed 3 times with distilled water. Physisorption of PAH to the nanofibre surface made the nanofibres positively charged. Next, the PAH coated nanofibres were immersed in a 0.5 mg/ml aqueous solution of Collagen I Rat Tail Protein for 15 minutes and rinsed with PBS solution. Finally, the modified substrates were stored in PBS before further use.

1.c. Culturing or Collecting Cells in the Cell Culture Substrates for Photoporation Treatment HeLa cells (#CCL-2) and Jurkat clone E6.1 (#TIB-152) were obtained from ATCC (American Type Culture Collection) and employed as model for the transfection of respectively adherent and suspension cells by photoporation. Human lung epithelial cells (H1299) stably expressing enhanced green fluorescent protein (eGFP) were used for the validation of siRNA knockdown experiments. HeLa cell culture medium was made from DMEM/F-12 with 2 mM glutamine, 100 U/mL penicillin/streptomycine and 10% heat-inactivated fetal bovine serum (FBS). H1299 and Jurkat cell culture medium consisted of RPMI1640 with 2 mM glutamine, 100 U/mL penicillin/streptomycine and 10% FBS.

To grow adherent cells, cell culture substrates were placed in 6-well titer plates (#10062-892, VWR) to which HeLa or H1299 were added (~1×10$^6$ cells in 2 ml cell culture medium). Cells were allowed to attach and grow during 24 hours in a cell incubator at 37° C. in a humidified atmosphere with 5% $CO_2$. Just prior to photoporation treatment, the molecules of interest that need to be delivered into the cells were added to the cell medium.

Jurkat cells were cultured in 75 $cm^2$ or 175 $cm^2$ flasks (#734-2313, #734-2315, VWR®) at a cell density between 1×10$^5$ and 1×10$^6$ cells/ml. For photoporation, the molecules of interest were added to the cell medium and cells were transferred to the cell substrates at ~2×10$^5$ cells/well. Cells were allowed to sediment on the fibre web during 5 minutes before starting the photoporation laser scanning.

Final experiments were performed on human T cells, which were obtained from Ghent University hospital. Buffy coats were obtained from healthy donors. Periperheral blood mononuclear cells (PBMCs) were isolated via density centrifugation using Lymphoprep (Alere Technologies, Oslo, Norway). Next, PBMCs were incubated in IMDM (Gibco, Invitrogen, Merelbeke, Belgium) supplemented with 10% fetal calf serum ((FCS, Bovogen), 100 U/ml penicillin (Gibco, Invitrogen), 100 µg/ml streptomycin (Gibco, Invitrogen), 2 mM glutamine and 5 ng/ml IL-2 (Roche, Vilvoorde, Belgium) and stimulated with CD23/CD28 beads (Stemcell Technologies, Vancouver, Canada r) at a 1:1 bead to cell ratio. After 7 day the cells were harvested and re-incubated with X-ray irradiated (40 Gy) (SARRP) PBMCs (1:2 ratio) and X-ray irradiated (50 Gy) JY (5:1 ratio) feeder cells in complete IMDM supplemented with 1 µg/ml phytohemagglutinin (Remel Europe, KENT, UK). After an additional 14 days, CD3+ cells were harvested and used for experiments as further indicated. Feeder cells were irradiated using the Small Animal Radiation Research Platform (Xstrahl, Surrey, UK). For photoporation treatment, T-cells were transferred to the culture substrates at a density of ~8×10$^5$ cells/well and already in the presence of the transfection molecules. Cells were allowed to sediment on the fibre web for 5 minutes before starting the laser treatment.

1.d Photoporation of Adherent Cells

The method according to the present invention is schematically illustrated in FIG. 1. First, a structure comprising material and particles able to absorb electromagnetic radiation is provided (FIG. 1a.). The structure is for example synthesized as described above. Subsequently, cells are grown on the structure for example as described above (FIG. 1b.). The cells are photoporated using a custom-built optical set-up as previously reported with some minor modifications (R. H. Xiong et al., Comparison of Gold Nanoparticle Mediated Photoporation: Vapor Nanobubbles Outperform Direct Heating for Delivering Macromolecules in Live Cells, Acs Nano, 8 (2014) 6288-6296) (FIG. 1c.). Briefly, a pulsed laser with 7 ns pulse duration was tuned at a wavelength of 647 nm (Opolette™ HE 355 LD, OPOTEK Inc, CA) and applied to irradiate the structure comprising nanofibres and IONP. The collimated pulsed laser beam was directed through a 1° Light Shaping Diffuser (Physical Optics Corporation, Torrance, CA), which in combination with an achromat lens in front of the microscope entrance and a 10× objective lens (Plan Fluor, Nikon) resulted in a laser beam diameter of ~250 µm at the sample. The laser pulse energy was monitored by an energy meter (J-25MB-HE&LE, Coherent) synchronized to the pulsed laser. In order to scan all the cells on the structures comprising nanofibres and IONP according to the present invention (diameter of ~9 mm), a motorized microscope stage was used to scan the sample through the stationary laser beam. As the laser repetition rate was 20 Hz, the scanning speed was set at 3 mm/s with a distance between subsequent line of 0.15 mm. In this way, all cells received at least one laser pulse up to maximally 4 in the overlapping regions between neighboring irradiation zones. In some experiments with Jurkat or human T-cells, the cells were scanned multiple times, as indicated in the main text. In that case the cells were re-suspended within the well and allowed to sediment again between each scan in order to let the cells randomly attach to the nanofibres at new locations. The transfected cells are shown in FIG. 1d.

1.e Intracellular Delivery of Molecules by Photoporation

Figure 2:
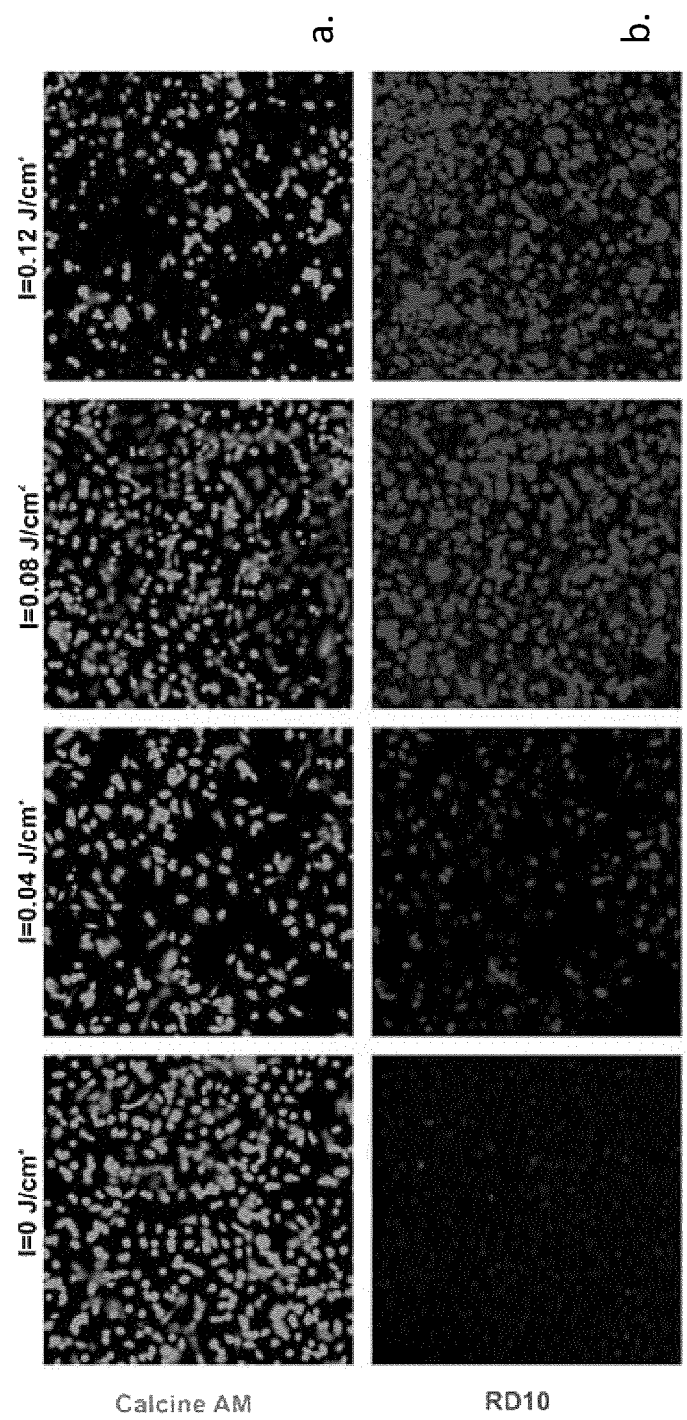
FIG. 2 shows confocal images showing the calcein-AM viability staining and intracellular delivery of red fluorescently labelled dextran of 10 kDa (RD10) with a single 7 ns laser pulse of increasing fluence.

To evaluate the intracellular delivery by photoporation of a structure according to the present invention, red fluorescently labelled dextran of 10 kDa (RD10) was added to HeLa cells cultured in a structure comprising nanofibres and 0.23 vol % ION P. Cells were scanned with a 7 ns pulsed laser beam (λ=647 nm) as described above. After laser treatment, cells were washed and the Calcein AM viability stain was added to the cells. Exemplary confocal images using different laser fluences are shown in FIG. 2. FIG. 2a shows confocal images showing green fluorescence from the calcein AM viability staining and indicates that cell toxicity only became obvious for the highest laser fluence of 0.12 J/cm². FIG. 2b shows confocal images showing red fluorescence from RD10, and indicates an increasing intracellular delivery of RD10 with increasing laser fluence.

Figure 3:
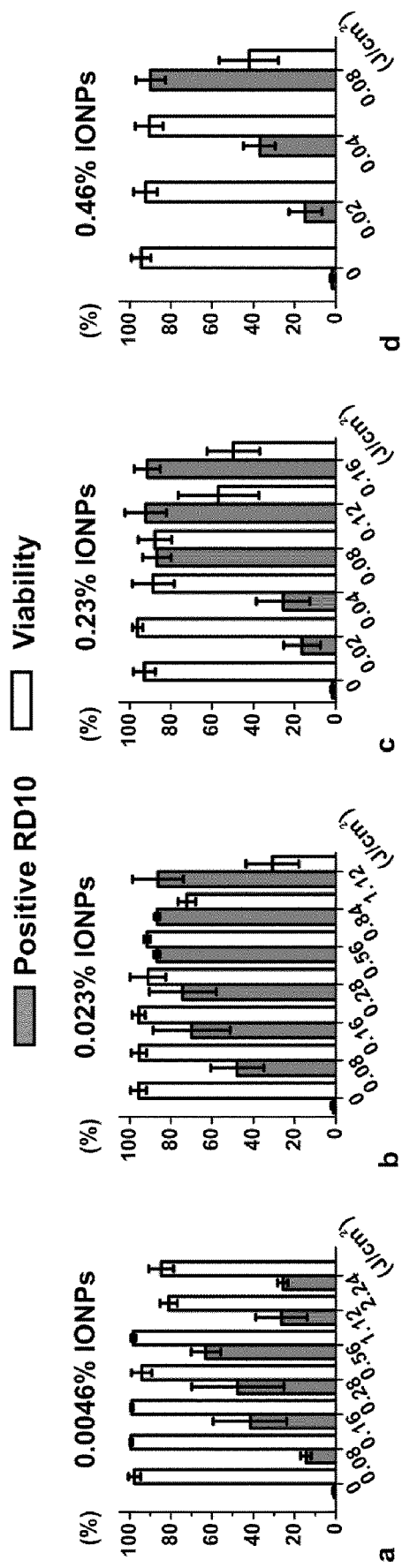
FIG. 3 shows the delivery efficiency of red fluorescently labeled 10 kDa dextran (RD10) and cell viability (Calcein positive cells) using different laser pulse fluences and concentrations of iron oxide nanoparticles (IONP)

Intracellular delivery of RD10 and cell viability were systematically evaluated by confocal microscopy for various laser fluences and structures prepared with different IONP concentrations (FIG. 3). Delivery efficiency was quantified as the percentage of RD10 positive cells, while viability was expressed as the percentage of Calcein positive cells. As expected, in the absence of laser irradiation (0 J/cm²), no noticeable RD10 uptake occurred into HeLa's. Upon applying laser irradiation, RD10 was successfully delivered into cells to an extent that depended on the applied laser fluence and IONP content. Increasing the laser fluence or IONP content generally lead to more intracellular delivery, although cell toxicity gradually increases as well. Interestingly, it was found that there are several combinations of laser fluences and IONP concentrations that lead to optimal delivery efficiencies. For example, for the structures with the lowest IONP content of 0.023 vol % (corresponding to 3.6 IONP/cell) a laser fluence of 0.56 J/cm² gave >85% positive cells with ~87% cell viability. This is virtually identical to what was obtained with the structures with 0.23 vol % IONP (43 IONP/cell) but with an almost 7× lower laser fluence of 0.08 J/cm².

1.f Repeated Activation of Structures for Transfection of Cells

Nanoparticle sensitized photoporation methods known in the art use nanoparticles as for example gold nanoparticles which can be activated only once because they tend to fragment after the first laser pulse, resulting in a loss of their photothermal functionality. However, aimed at improving the delivery efficiency even further, multiple irradiation cycles of a structure according to the present invention was evaluated.

Figure 4:
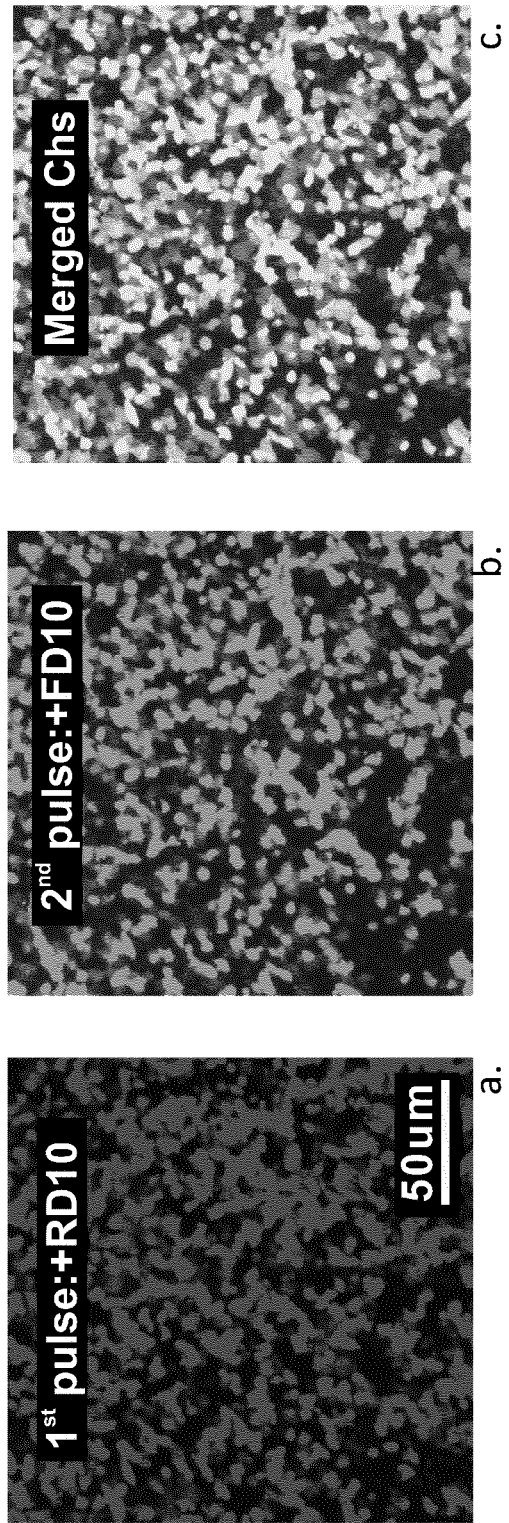
FIG. 4 shows confocal images in case of repeated photoporation first with red fluorescent 10 kDa dextran (RD10) followed by green fluorescent FITC-dextran (FD10)

Cells on a structure comprising nanofibres and IONP according to the present invention were irradiated two times. In the first round RD10 was delivered as mentioned before. The cells were washed subsequently. FIG. 4a shows a confocal image after the first round. Then the cells were irradiated a second time on the same structure now in the presence of 10 kDa green fluorescent FITC-dextran macromolecules (FD10). Confocal image after the second round is given in FIG. 4b. The overlay of FIG. 4a and FIG. 4b is shown in FIG. 4c and indicates that many cells show both green and red fluorescence.

Figure 5:
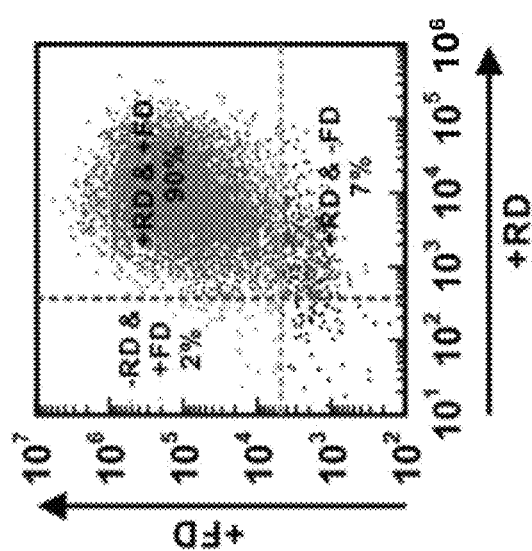
FIG. 5 shows flow cytometry data in case of repeated photoporation with RD10 and FD10 showing that 90% of cells contain both RD10 and FD10.

Quantitative analysis by flow cytometry given in FIG. 5 confirmed that 90% of cells were positive for both RD10 as FD10.

Figure 7:
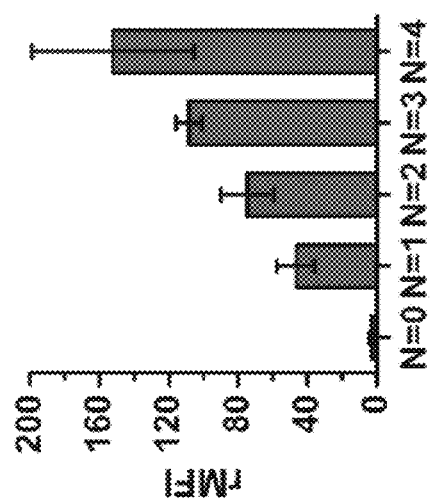
FIG. 7 shows the average relative mean fluorescence intensity (rMFI) per cell with increasing number of photoporation steps in case of consecutive photoporation of HELA cells with FD10.
Figure 6:
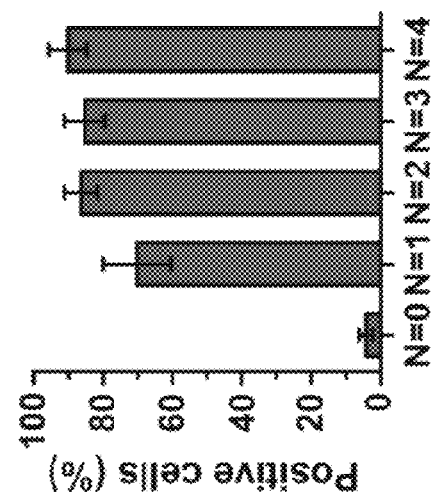
FIG. 6 shows the delivery efficiency in case of consecutive photoporation of HELA cells with FD10, doubling its concentration between each photoporation step (N=1 to 4)

To provide further evidence of repeated photoporation using the same structure, HELA cells were photoporated up to 4 times with FD10. The FD10 concentration was doubled (from 0.2 mg/ml to 1.6 mg/ml) between each photoporation round to more easily see the increase in intracellular delivery (which is diffusion driven, thus requiring a concentration gradient). The percentage of positive cells after each photoporation is given in FIG. 6. The relative mean fluorescence intensity per cell after each photoporation is given in FIG. 7. While the percentage of positive cells increased from ~70% to ~90% (FIG. 6), the increased delivery was most apparent from the relative mean fluorescence per cell (rMFI) which increased almost linearly with each additional round of photoporation (FIG. 8).

1.g Intracellular Delivery of Large Macromolecules by Photoporation

To evaluate the intracellular delivery of larger macromolecules, i.e. molecules having a the molecular weight of proteins or mRNA, 40 kDa, 70 kDa, 150 kDa and 500 kDa FITC-dextran (FD40, FD70, FD150 & FD500) molecules were delivered in HeLa cells by 1×, 2× and 4× photoporation. Uptake was determined by flow cytometry and expressed as the percentage of positive cells (FIG. 8) and rMFI (FIG. 9).

Figure 8:
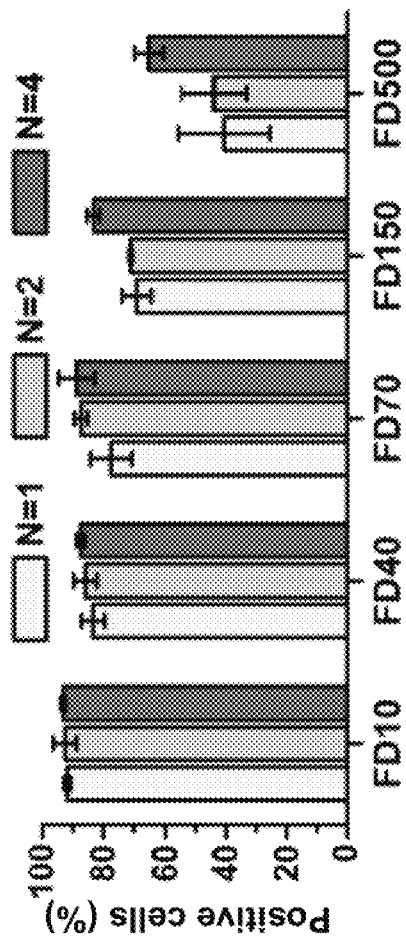
FIG. 8 shows the delivery efficiency of FITC-dextran molecules of various molecular weights (10, 40, 70, 150 and 500 kD) for increasing number of photoporations (N=1, 2, 4)
Figure 9:
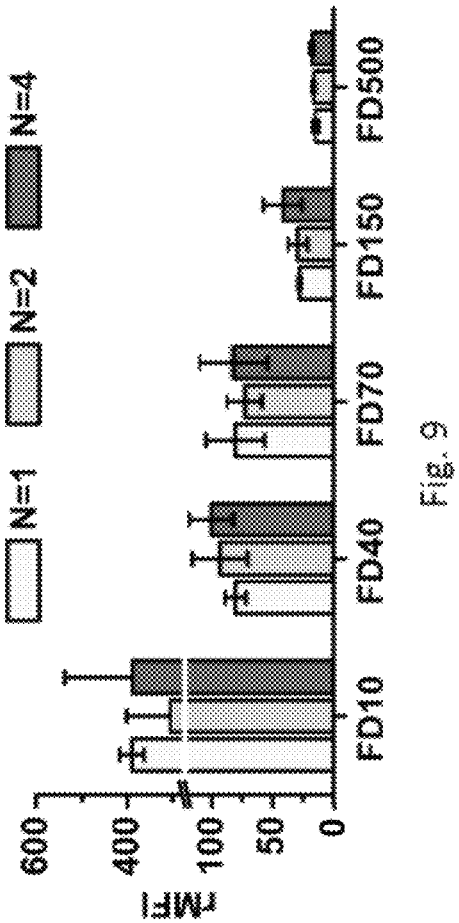
FIG. 9 shows the relative mean fluorescence intensity (rMFI) per cell for different FITC-dextran molecules with increasing number of photoporations.

As shown in FIG. 8 and FIG. 9, delivery efficiency gradually decreased for increasing molecular weight, which is due to a combination of molecules becoming large compared to the pore size as well as slower molecular diffusion. Repeating the photoporation procedure generally resulted in slightly more positive cells, while it did not improve the amount delivered per cell on average.

From FIG. 8 and FIG. 9, it can be concluded the method according to the present invention is successful in transfecting cells with compounds up to at least 500 kDa, with a percentage of transfected cells ranging between 65 and 90%, depending on the molecular size.

1.h Transfection of Suspension Cells by Photoporation

To investigate to which extent the method according to the present invention is successful in transfecting suspension cells, Jurkat cells (an immortalized line of human T lymphocytes which is a widely used model for hard-to-transfect primary human T cells) were used. 2 mg/ml FD10 was first added to the Jurkat cell suspension before adding the cells to the structures comprising nanofibres and IONP. Cells were allowed to sediment for 5 minutes, which was sufficient to collect them on top of the fibre web. After that, they were photoporated by scanning of the laser beam in exactly the same manner as for adherent cells. The available number of IONP clusters per cell was quantified by multiplying the Jurkat cell area with the IONP density, which in this case ranged from 7.7 to 28.4 IONP/cell.

Figure 10:
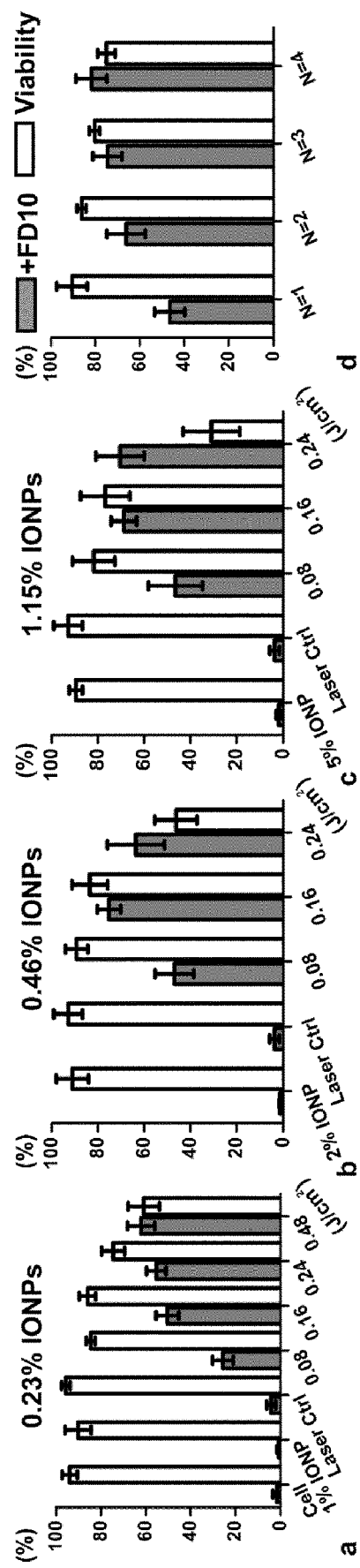
FIG. 10 shows the delivery efficiency and viability of FD10 in Jurkat cells for a structure comprising fibres having different concentrations of IONP and irradiated with a laser pulse of different fluence.

Next the transfection efficiency as a function of laser fluence and IONP content was investigated. As shown in FIG. 10a, FIGS. 10b and 10c, the delivery efficiency increases with increasing laser fluence at the expense of cell viability as measured by the calcein red-orange AM viability stain. Similarly, the delivery efficiency generally increased when increasing the IONP content for a given laser fluence. Setting a threshold of minimal 80% viability, the best transfection efficiency (~75% positive cells) was obtained for a structure comprising nanofibres and 0.46 vol % IONP (~12 IONP/cell) and a laser fluence of 0.16 J/cm². Finally, repeated photoporation was tested (FIG. 10d), again finding that the percentage of positive cells could be increased by repeating the procedure with only little effect on cell viability. Note that for this experiment a structure comprising nanofibres and 0.46 vol % IONP with a suboptimal laser fluence of 0.08 J/cm² was used to better show the gradual improvement. Cells were gently resuspended between subsequent laser scans and allowed to sediment again so that they randomly attach to the nanofibres at new locations.

1.i ICP-MS Measurement to Detect Possible Leakage of IONP from the Structure Comprising Nanofibres and IONP Upon Laser Irradiation To evaluate whether there was direct contact between the particles able to absorb electromagnetic radiation embedded in the material of the structure and the cell, the iron content of cells after photoporation was measured by ICP-MS (Inductively Coupled Plasma Mass Spectrometry).

Irradiation of the structure comprising nanofibres and IONP was done with and without the presence of cells on the fibres. In the absence of cells, distilled water was added to the structures comprising nanofibres and particles. The distilled water was collected again after laser treatment for ICP-MS analysis. Samples with cells were prepared as described above. After laser irradiation, the cells were collected by washing with PBS in case of suspension cells, or trypsinized in case of adherent cells. Finally, 100 μl aqua regia (3:1 mixture of hydrochloric acid with nitric acid) was added to the samples for digestion of cells or other organic matter that may be present. Next, the iron content was measured by ICP-MS (Agilent 8800, Santa Clara, CA, USA). Specifically, sample solutions were diluted 100 times in metal-free tubes, adding Y as internal standard (at a final concentration of 1 μg $L^{-1}$) to correct for instrument instability and/or signal drift, to a final volume of 10 mL with 2% HNO3. External calibration standards (0, 0.5, 1, 2.5, 5 and 10 μg $L^{-1}$ Fe+1 μg L−1 Y) were prepared from a 1,000 mg $L^{-1}$ Fe standard stock solution by diluting appropriate amounts using a slightly acidic solution (2% $HNO_3$), hereby mimicking the matrix of the sample solutions. During all steps of the sample preparation the solutions were mixed thoroughly using a vortex mixer.

The internal standard correction was performed according to the following equation:

$$R_{Fe,corr} = \frac{R_{Fe}}{R_Y}$$

with $R_{Fe,corr}$ the corrected $^{56}Fe(NH_3)_2^+$ signal response, $R_{Fe}$ the measured $^{56}Fe(NH_3)_2^+$ signal response and $R_Y$ the $^{89}Y(NH_3)_6^+$ signal response. The relative standard deviations were calculated via error propagation for all calculation steps (internal standardization and external calibration). Background equivalent concentrations (BEC) were calculated instead of limits of detection/quantification (LODs/LOQs) since the BEC is a more representative measure for the analytical performance as background concentrations for Fe are typically slightly elevated.

Figure 12:
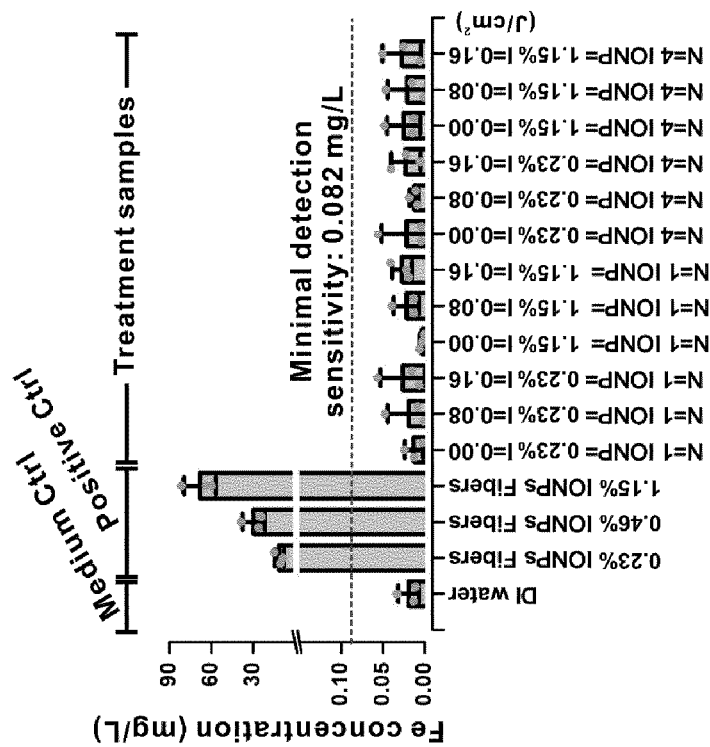
FIG. 12 shows the iron concentration measured by ICP-MS in distilled water (negative control) in fibres with different concentrations of IONP digested by aqua regia (positive control) digesting an amount of fibres comparable to a culture well with different concentrations of IONP, and in distilled water collected from the structure after photoporation.
Figure 11:
FIG. 11 shows the iron concentration measured by ICP-MS in untreated cells (negative control), cells incubated with IONP (positive control) and cells treated by photoporation with a structure composed of fibres containing different concentration of IONP.

HeLa and Jurkat cells were photoporated as described above using a structure comprising nanofibres and 0.23 vol % or 0.46 vol % IONP, respectively. As a positive control cells incubated with 500 μg/ml of 30 nm IONP coated with polyethylene glycol for 4 hours at 37° C. were included as well. As shown in FIG. 11, the positive control indeed had a significantly higher iron concentration in comparison with the negative control (untreated cells) for both cell types. Importantly, however, the iron content in the photoporated cells did not differ significantly from untreated cells for any of the tested laser fluences (0.08-0.16 J/cm²) or number of laser scans (up to N=4). While this proves that there is no measurable increase in iron content in cells, one could argue that the endogenous iron content in cells is already fairly high so that small increases may not be easily detected. Therefore, the potential iron release from the structure according to the present invention when submerged in pure distilled water and irradiated with laser light (without any cells present) was evaluated. The results in FIG. 12 show that the iron content in distilled water after laser activation of the structures comprising nanofibres and IONP had not significantly increased and remained below the instrument's detection sensitivity of 0.082 mg/L. This was not only true for structures comprising nanofibres and 0.23 vol % IONP, but as well for those with the highest IONP content of 1.15 vol % even after multiple laser activation cycles (up to N=4) with a fluence up to 0.16 J/cm². As a positive control a similar amount of fibres as is present in a structure comprising nanofibres was digested with aqua regia, which should release all of the IONP. In that case ICP-MS indeed detected very high iron concentrations proportional to the embedded IONP content (0.23 vol %, 0.46 vol % or 1.15 vol % IONP). It can be concluded the structures according to the present invention reach the intended goal of efficient cell transfections upon laser activation while avoiding any direct exposure of cells to potentially toxic sensitizing nanoparticles or its constituents.

1.j Efficient Gene Silencing in Adherent Cells by Photoporation

Figure 13:
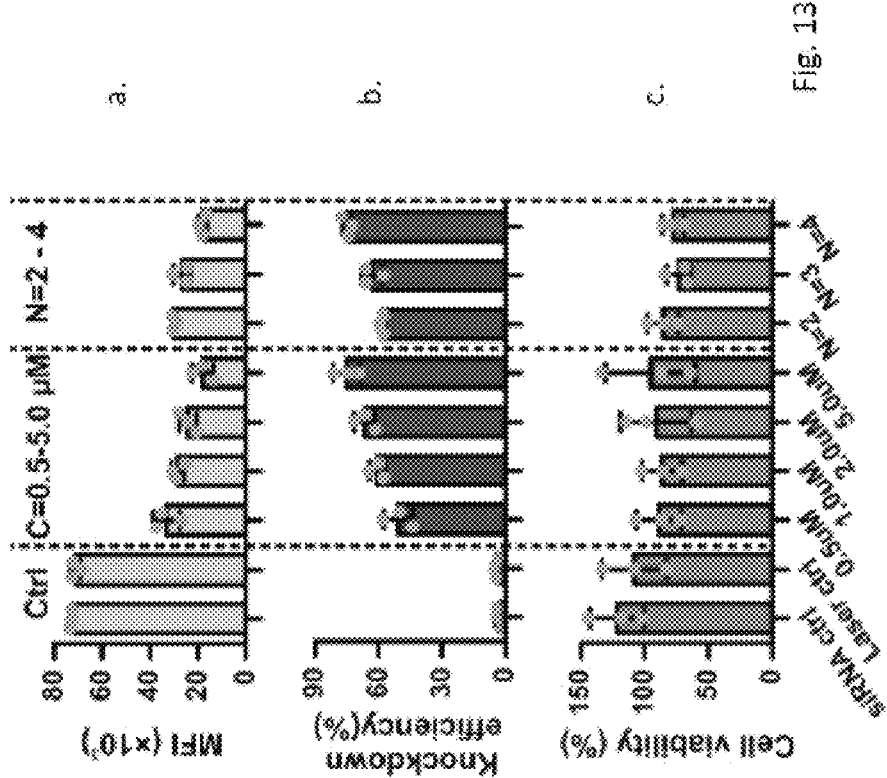
FIG. 13 shows the MFI, knockdown efficiency and cell viability of H1299 cells stably expressing GFP and grown on fibre substrates after N repeated photoporations (N=1-4), the fibre substrates comprise IONPs with different concentrations C of siRNA (C=0.5-50 µM)

To evaluate the intracellular delivery of siRNA as a functional macromolecule anti-eGFP siRNA was delivered into adherent H1299 cells which stably express green fluorescence protein (GFP). Cells were grown on collagen-coated nanofibres webs having 0.23 vol % IONP at 37° C. for 24 h, after which they were photoporated (0.08 J/cm²) with control and anti-GFP siRNA, and allowed to continue to grow for 24 h before measuring GFP expression. Examination by confocal microscopy of a trial experiment with 5 μM siRNA showed clear GFP downregulation when treated with anti-GFP siRNA but not with control siRNA. Flow cytometry confirmed these results, with 77% GFP positive cells when treated with the control siRNA, which decreased to 28% after treatment with the functional siRNA. Knockdown efficiency and cytotoxicity as a function of the siRNA concentration (0.5, 1, 2 and 5 μM) was systematically evaluated. eGFP expression decreased for higher siRNA concentrations, reaching 75% of cells with significant gene silencing with 5 μM siRNA (FIGS. 13a, 13b). It was evaluated if repeated photoporation could be beneficial for siRNA gene silencing as well. Indeed, repeating the laser scanning up to 4 times with each scan, eGFP expression gradually decreased with the knockdown efficiency reaching up to 75% after 4 repeated laser irradiations. For all conditions the cell viability, here measured by the cell Titer-Glo luminescent assay, remained very good (>75%, FIG. 13b).

12.k Efficient Gene Silencing in Primary Human T-cells by Photoporation

Figure 14:
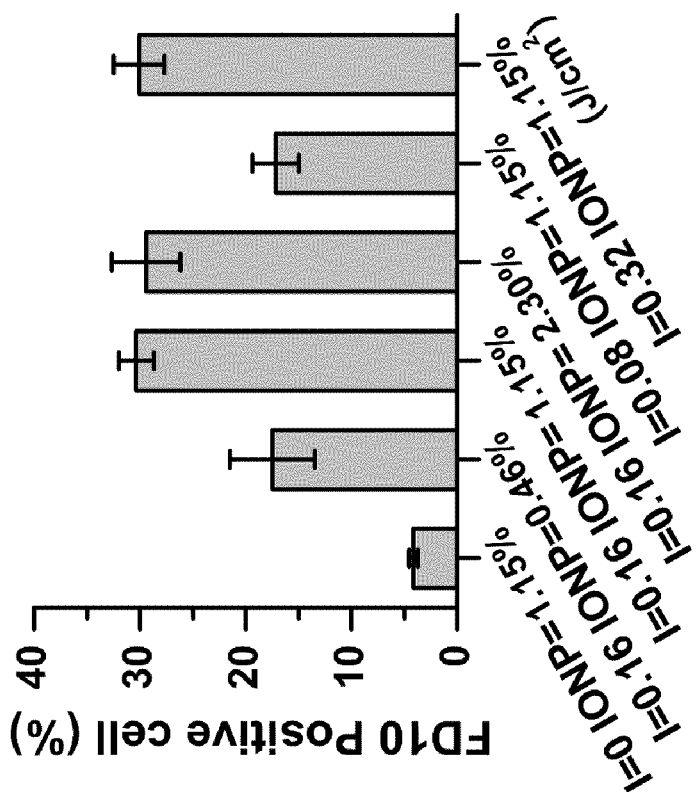
FIG. 14 shows the intracellular delivery of FD10 in human T cells by photoporation using different IONP concentrations and laser fluences.
Figure 15:
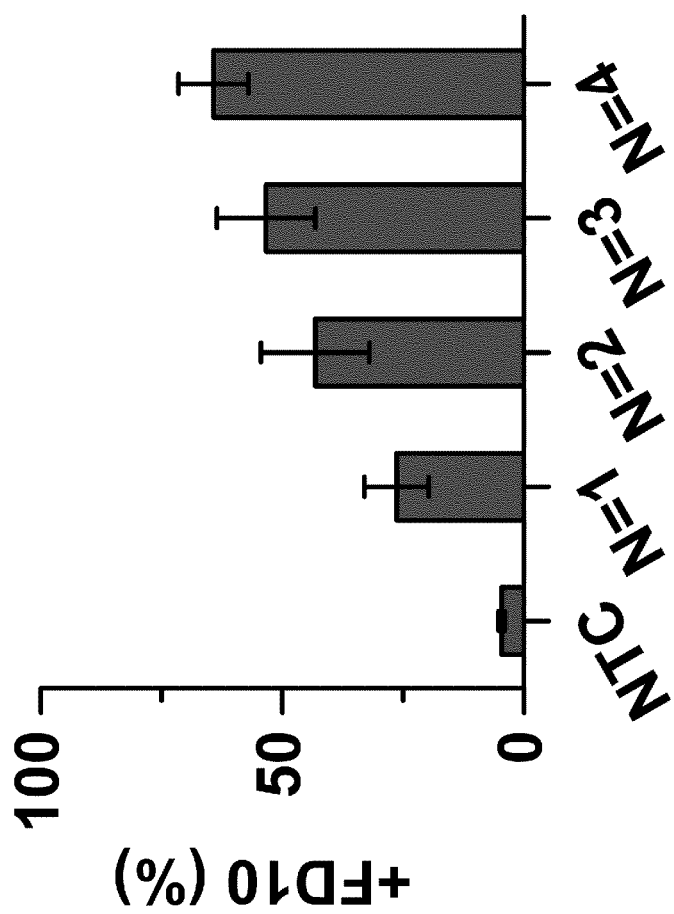
FIG. 15 shows the intracellular delivery of FD10 in human T cells in case of repeated photoporation (N=1 to 4)

The photoporation of human patient derived CD3+ T-cells on a structure comprising nanofibres and IONP according to the present invention was evaluated. Structures with 0.23 vol %, 1.15 vol % and 2.3 vol % IONP were prepared and T cells were transfected with a fixed laser fluence of 0.16 J/cm² (as this was the optimum for Jurkats). The best transfection efficiency (~30% positive cells) was obtained with 1.15 vol % IONP (FIG. 14). Next we optimized the laser fluence, confirming that the transfection efficiency was optimal at 0.16 J/cm². Interestingly, increasing the laser fluence to 0.32 J/cm² did not improve transfection efficiency further as predicted by our theoretical simulations. Similar to Jurkats, repeated photoporation did improve the percentage of FD10 positive cells (FIG. 15). For instance, for three times photoporation a transfection efficiency of 53% was achieved with a cell viability of >60%. Based on these results we selected I=0.16 J/cm², 1.15 vol % IONP neutral nanofibres, and N=3 for further experiments on human T cells.

Figure 16:
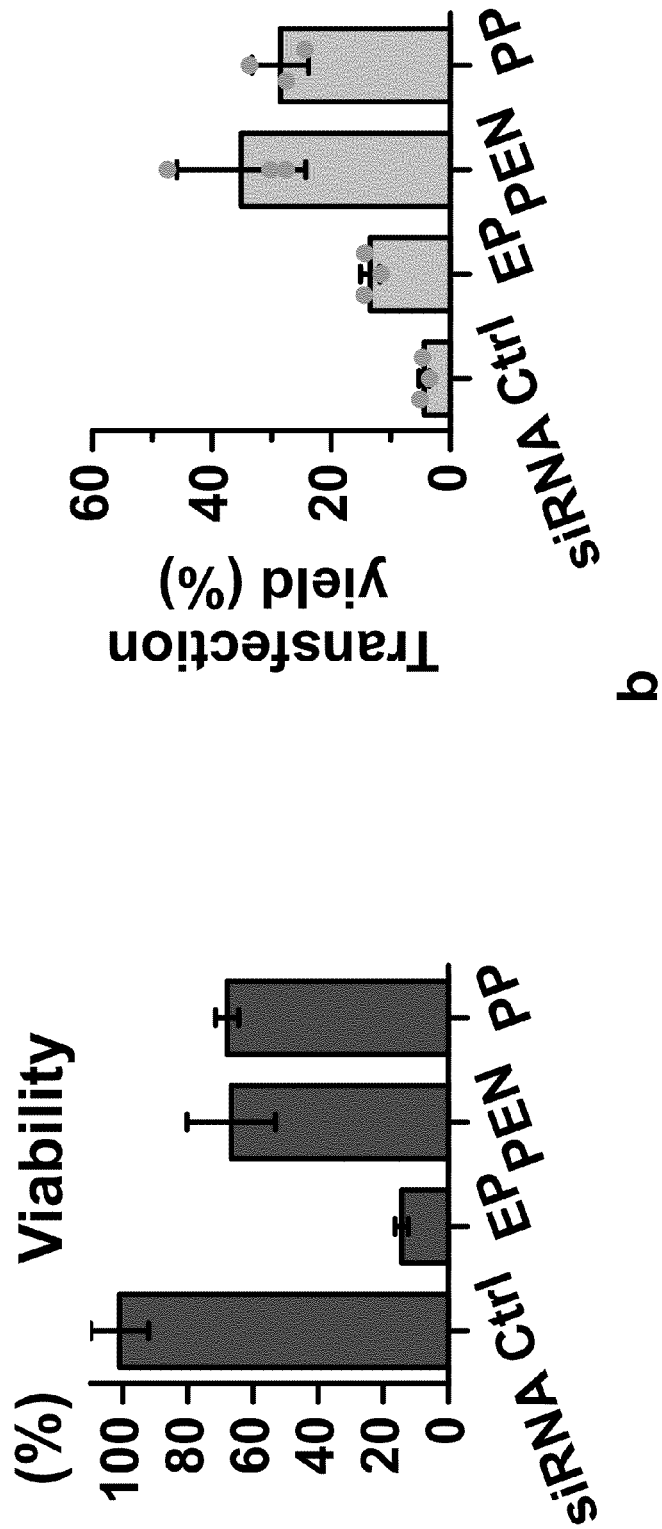
FIG. 16 shows the siRNA delivery performance in stimulated human T cells using electroporation (EP), photoporation according to the present invention (PEN) and gold nanoparticle sensitized photoporation (PP) showing the viability (FIG. 16a) and the transfection yield (FIG. 16b), with the transfection yield being the percentage of living and transfected cells obtained by multiplying the percentage of positive cells with the percentage of living cells.

The siRNA delivery performance of photoporation in stimulated human T cells was tested with a fluorescently-labelled model siRNA (without biological function). A direct comparison was performed with two other more established physical transfection techniques, being electroporation and traditional gold nanoparticle sensitized photoporation. In FIG. 16 electroporation is referred to as EP, photoporation according to the present invention is referred to as PEN and gold nanoparticle sensitized photoporation is referred to as PP. As is frequently observed for electroporation, only few cells survived the treatment (14.2%, FIG. 16*b*) which were, however, almost all positive for siRNA (94.2%, FIG. 16*a*). The product of both measurements is the so-called transfection yield, i.e. the percentage of living and transfected cells, which amounted to only 13.5% for electroporation. Both gold nanoparticle sensitized photoporation and photoporation using a structure according to the present invention were much more gentle to the cells with cell viabilities >60% and 40-50% positive cells. This resulted in a transfection yield of 35% for photoporation using a structure according to the present invention and 30% for gold nanoparticle sensitized photoporation (FIG. 16*b*). As such it can be concluded that the transfection yield with photoporation according to the present invention is more than 2.5× better than for electroporation, while it is similar to traditional photoporation. The latter is an astounding achievement given the fact that this is obtained without direct contact between particles and cells according to the present invention.

Figure 18:
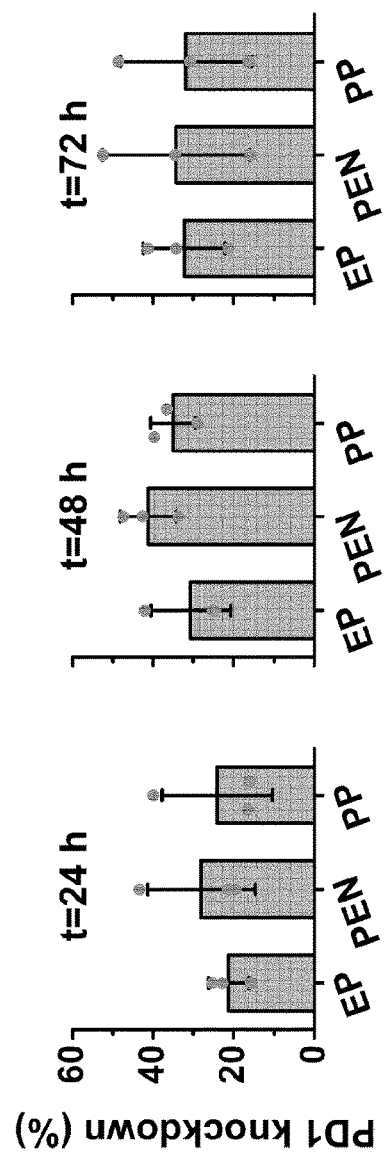
FIG. 18 shows the level of PD1 knockdown in human CD3 T cell with siRNA up to 72 hours after delivery by electroporation (EP), photoporation according to the present invention (PEN) and gold nanoparticle sensitized photoporation (PP)
Figure 17:
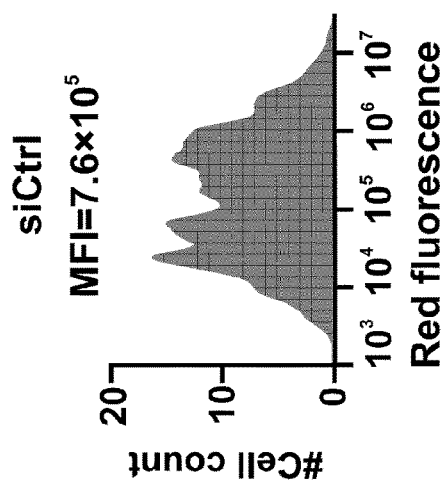
FIG. 17 shows an exemplary histogram showing PD1 expression in CD3+ T cells.

To evaluate gene silencing with functional siRNA the PD-1 receptor was targeted. On the first day T-cells were collected from donors and stimulated for a first time. After 7 days, cells were collected for transfection with siRNA and stimulated a second time. Cells were transfected with 1 μM siPD1 and PD1 expression was quantified 24 hours, 48 hours and 72 hours later by flow cytometry after PD-1 antibody staining. Transfection was again compared between electroporation, photoporation and gold nanoparticle sensitized photoporation. Exemplary flow cytometry histograms are shown in FIG. 17, k for cells 48 hours after photoporation with control siRNA and siPD1, showing a reduction in PD1 expression in the latter case. From the decrease in PD-1 antibody staining over the entire population of living cells the knockdown efficiency was quantified over time (FIG. 18). A similar level of PD-1 gene silencing was obtained for all three transfection methods, reaching up to ~40% knockdown after 48 h. Keeping in mind that photoporation has a 2.5× higher transfection yield than electroporation thanks to its reduced toxicity, it confirms that it is a very promising and effective transfection method for the production of engineered T-cells for adoptive T-cell therapy.

Figure 19:
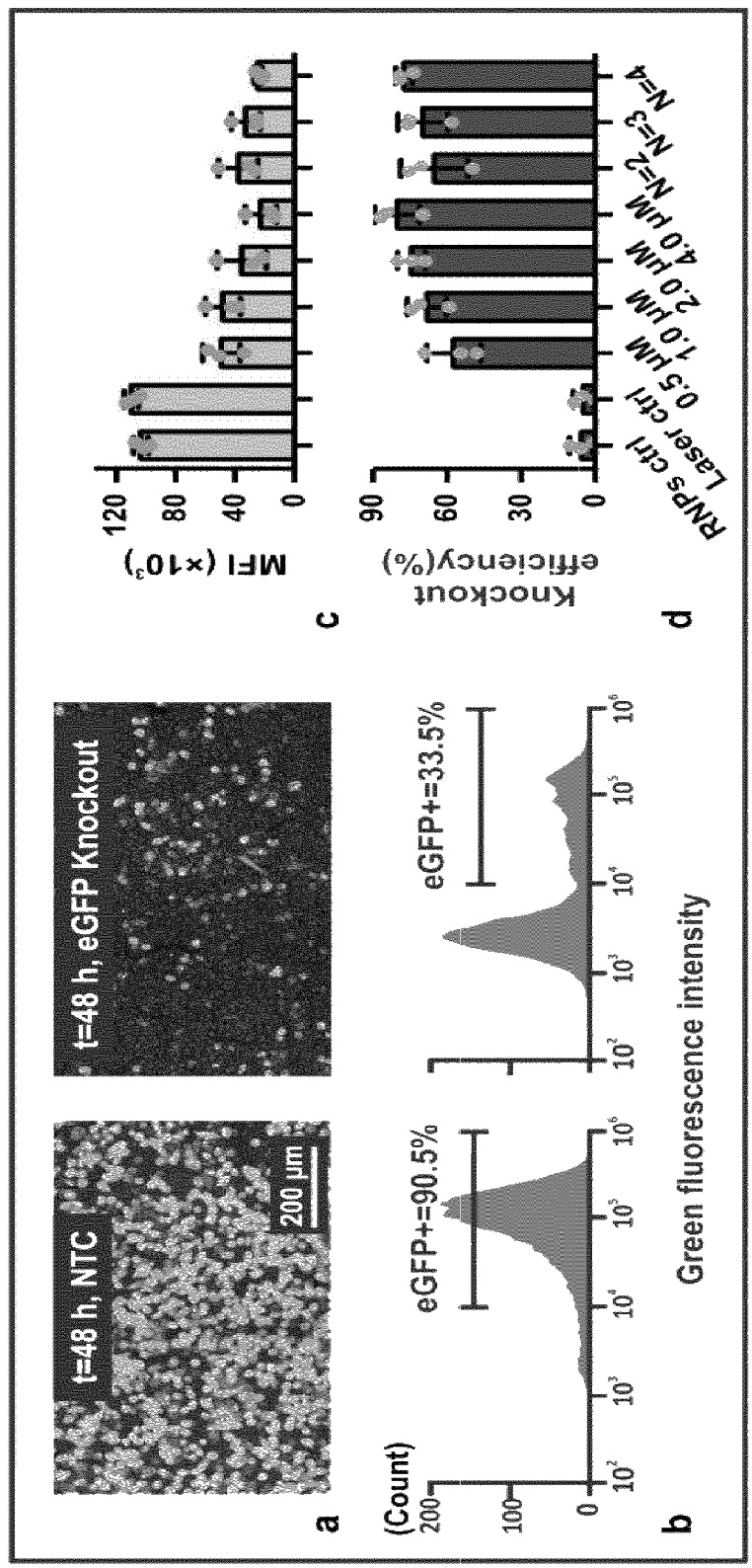
FIG. 19 shows the application of a structure comprising nanofibres from Polycaprolactone (PCL) with 1% IONPs for Cas-9 gene knockout in H1299.

FIG. 19 shows the application of a structure comprising nanofibres from Polycaprolactone (PCL) with 1% IONPs for Cas-9 gene knockout in H1299.

FIG. 19*a* shows confocal images showing green fluorescence in H1299 cells stably expressing GFP before (left) and after photoporation with 4 μM Cas-9 ribonucleoproteins designed to knock-out GFP expression (right). Samples were scanned once with a laser fluence of 0.08 J/cm$^2$.

FIG. 19*b* shows the corresponding cytometry histograms illustrating how eGFP expression is distributed over the cell population before and after photoporation with 90.5% and 33.5% eGFP positive cells, respectively. FIG. 19*c* and FIG. 19*d* show respectively the mean fluorescence intensity (MFI) and knockdown efficiency (=percentage of cells negative for eGFP) for H1299 cells that were photoporated with increasing concentration of Cas-9 ribonucleoproteins (0.5, 1, 2, 4 μM), as well as multiple times (N=2, 3, 4) with a concentration of 0.5 μM.

Figure 20:
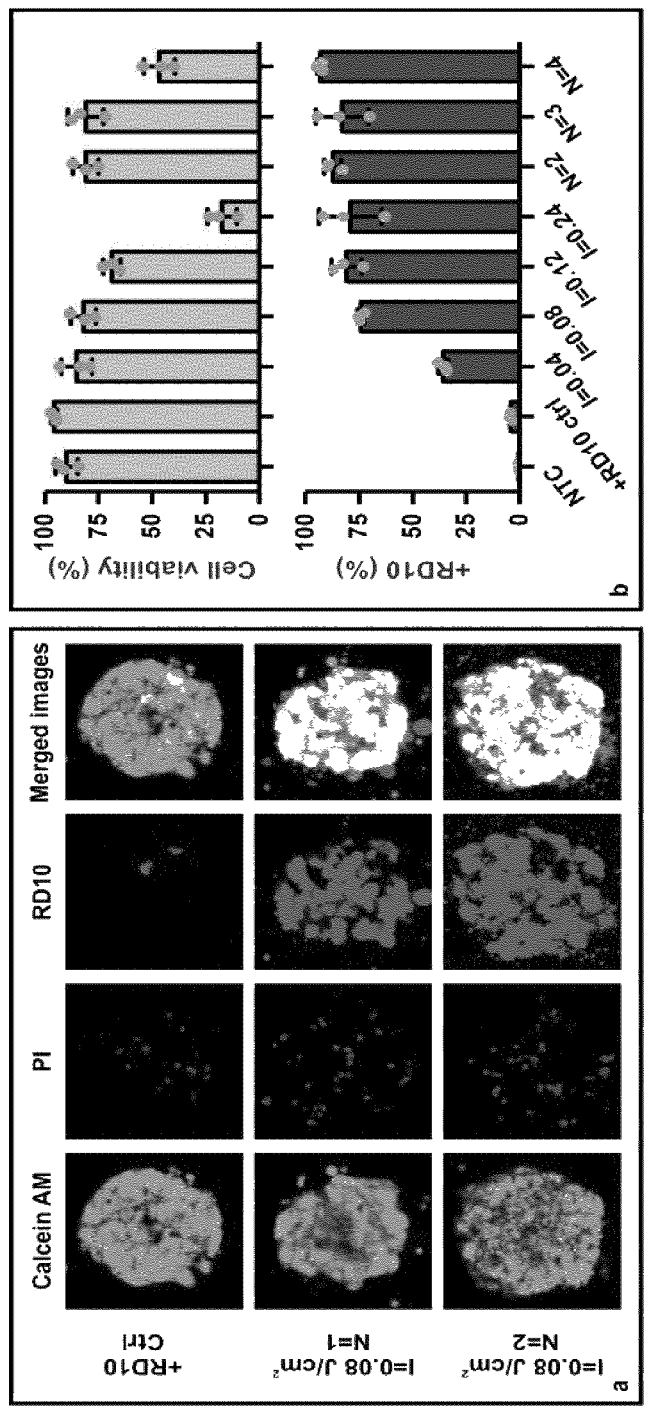
FIG. 20 shows the application of a structure comprising nanofibres from Polycaprolactone (PCL) with 1% IONPs for macromolecular delivery in H9 Human Embryonic stem cells.

FIG. 20 shows the application of a structure comprising nanofibres from Polycaprolactone (PCL) with 1% IONPs for macromolecular delivery in H9 Human Embryonic stem cells.

FIG. 20*a* shows confocal images showing successful delivery of fluorescently labeled dextran of 10 kDa (RD10) before (top row), after one photoporation cycle (second row) and after two photoporation cycles (bottom row). Live cells are stained with Calcein AM, while dead cells can be recognized by a positive propidium iodide (PI) signal. Photoporation was performed using a laser fluence of 0.08 J/cm$^2$.

FIG. 20*b* shows the cell viability and the percentage of RD positive cells quantified by imaging processing as a function of laser fluence (I=0.08, 0.12 and 0.24 J/cm$^2$) and multiple photoporation cycles (N=2, 3, 4).

Example 2 Non Porous Structure Comprising a Polymer Material and Nanoparticles

Figure 21A:
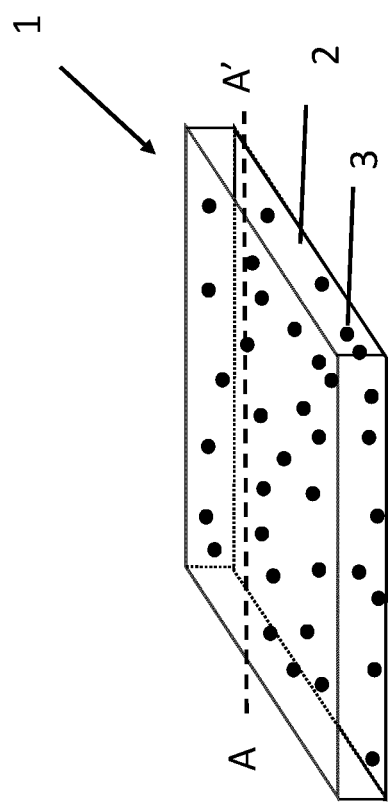
FIG. 21a and FIG. 21b show an alternative example of a structure to increase the permeability of a plasma membrane of cells comprising a polymer sheet.
Figure 21B:
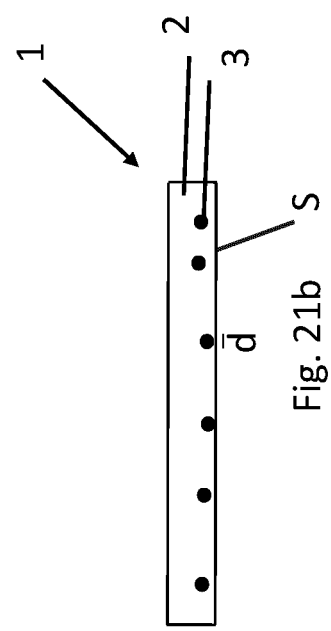

FIG. 21*a* shows a schematic illustration of an embodiment of a structure 1 according to the present invention. FIG. 21*b* shows the cross-section of the structure 1 shown in FIG. 21*a* along line A-A'. The structure 1 comprises a polymer sheet comprising a polymer material 2 and particles 3 able to absorb electromagnetic radiation. The particles 3 comprise for example carbon particles or iron oxide particles or a combination of carbon particles and iron oxide particles. The particles 3 are embedded in the material 2 and have for example an average equivalent spherical diameter d of 1000 nm.

The structure has a thickness t ranging between 0.1 μm and 100 μm and, for example a thickness of 1 μm, 2 μm or 5 μm.

The ratio of the free area surface S of the structure over the volume V of the structure, i.e. the ratio S/V, corresponds to 1/t.

The polymer sheet comprises preferably a polymer comprising or based on polystyrene, polycaprolacton, ethylcellulose, cellulose acetophthalate or polylactic-co-glycolic acid, cellulose, polyvinylalcohol, polyethylene glycol, gelatin, collagen, silk, alginate, hyaluronic acid, dextran, starch, polycarbonate or polyacrylate.

The particles are present in the material in a concentration ranging between 0.001 vol % and 20 vol % (volume particles/volume structure), for example in a concentration of 1 vol %, 2 vol % or 5 vol %.

Preferably, all or substantially all of the particles are completely embedded in the material of the structure, meaning that all or substantially all of the particles of the structure are completely surrounded by the material of the structure and that no particles or substantially no particles are exposed to the free area surface of the structure.

At least 60% of the particles present in the structure, are embedded in the material in such a way that the shortest distance L between this particles and the free area surface S of the structure ranges between 1 nm and 100 nm.

Figure 22:
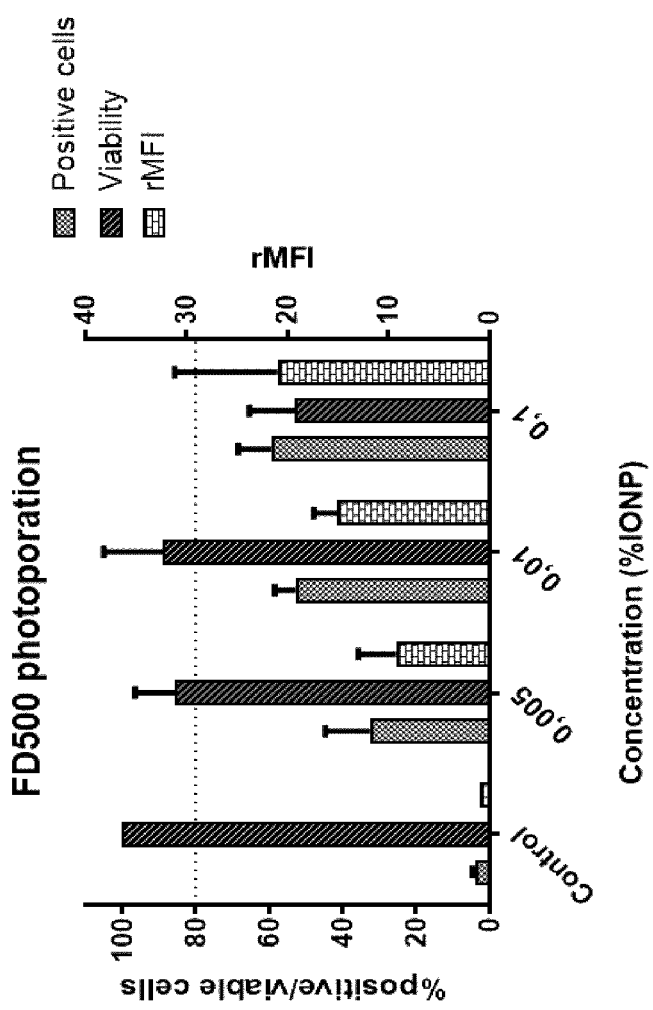
FIG. 22 shows the FD500 positive cells, the viability and the relative mean fluorescence intensity for photoporation of HeLa cells using polymer sheets having different concentrations of IONPs.

FIG. 22 shows the percentage of FD 500 (FICT-dextran of 500 kDa) positive cells, the viability of the cells measured via CellTiter Glo metabolic assay and the relative mean fluorescence intensity for photoporation of HeLa cells using a PLA film (2% PLA) having no IONPs (control), 0.005% IONP, 0.01% IONP and 0.1% IONP, were labeled.

Additionally, the percentage of FD500 positive cells, viability and relative mean fluorescence intensity (rMFI) was determined for photoporation (one photoporation cycle) of HeLa cells using a PLA film (2% PLA) with 0.025%

Figure 23:
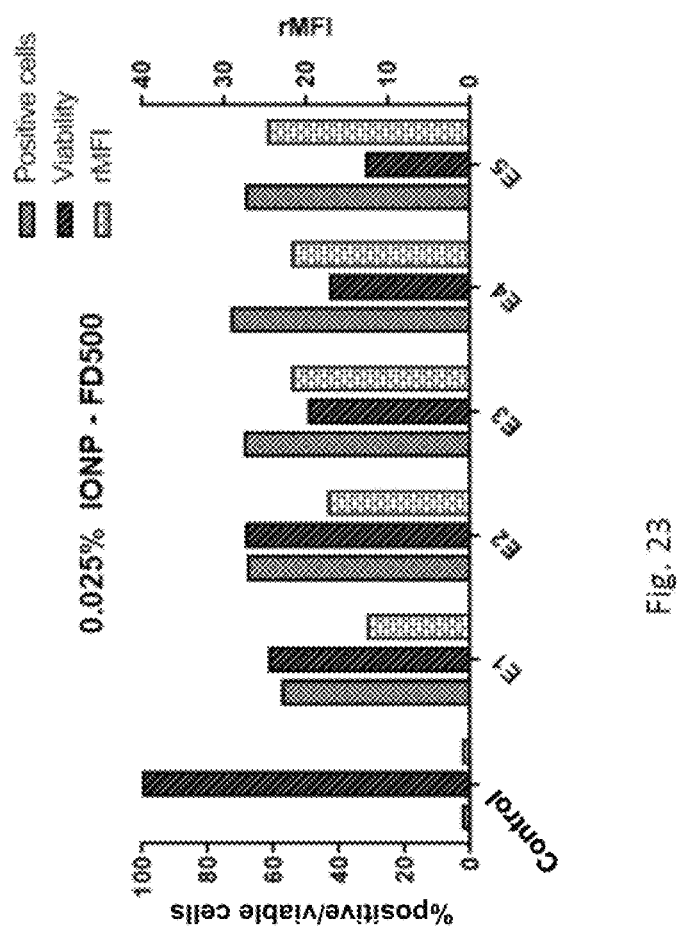
FIG. 23 shows the percentage of FD500 positive cells, the percentage of viable cells and the relative mean fluorescence intensity for photoporation of HeLa cells using polymer sheets having a particular concentration of IONPs using different laser fluences.

IONPs using different laser fluences, respectively 0.3 J/cm² (=E1), 0.5 J/cm²=E2)), 0.84 J/cm² (=E3), 1.26 J/cm² (=E4) and 1.6 J/cm² (=E5). The results are shown in FIG. 23.

The invention claimed is:

1. A method to increase the permeability of the plasma membrane of cells, said method comprising the steps of
providing a structure comprising a material and comprising particles able to absorb electromagnetic radiation embedded in said material, said particles having an average equivalent spherical diameter d, said structure defining a volume V and a free area surface S, said particles being present in said structure in a concentration ranging between 0.001 vol % and 20 vol % (volume particles/volume structure), at least P percent of said particles present in said structure being embedded in said material in such a way that the shortest distance L between said P percent of said particles and said free area surface S of said structure ranges between 1 nm and 500 nm; P being at least 60%,
introducing at least one cell on or at a distance of less than 100 µm from said structure; irradiating said structure with electromagnetic radiation.

2. The method according to claim 1, wherein said particles are present in said structure in a concentration ranging between 0.01 vol % and 5 vol %.

3. The method according to claim 1, wherein the surface density of particles positioned at a shortest distance L from said free area surface S of said structure with L ranging between 5 nm and 500 nm ranges between 104 prrr2 and 1/d2, with the surface density of particles being defined as the number of particles N present in said structure multiplied with said percent P of said particles being positioned at said shortest distance L from said free area surface divided by the free area surface of said structure (N·P/S).

4. The method according to claim 1, wherein at least 95% of said particles is not exposed to said free area surface of said structure.

5. The method according to claim 1, wherein said particles comprise particles selected from the group consisting of metal particles, metal oxide particles, carbon or carbon based particles and particles comprising one or more light absorbing compound and particles loaded or functionalized with one or more light absorbing compound.

6. The method according to claim 1, wherein said material comprises an inorganic material or an inorganic based material, a ceramic or ceramic based material, an organic material or organic based material, or a composite material comprising at least one of these materials.

7. The method according to claim 1, wherein said material comprises a material or a surface modified material with said material being selected from the group consisting of polystyrene, polycaprolacton, ethylcellulose, cellulose acetophthalate, polylactic acid, polylactic-co-glycolic acid, cellulose, polyvinylalcohol, polyethylene glycol, gelatin, collagen, silk, alginate, hyaluronic acid, dextran, starch, polycarbonate and polyacrylate.

8. The method according to claim 1, wherein said structure comprises a porous structure or a non porous structure.

9. The method according to claim 1, wherein said structure comprises a porous structure having a porosity of at least 50%.

10. The method according to claim 9, wherein said porous structures comprises fibres, particulates, a combination of fibres and particulates or a foam, with said particles being embedded in said fibres, said particulates or said foam.

11. The method according to claim 1, wherein said irradiating comprises irradiation with a pulsed radiation source having pulses having a duration in the range of 1 fs to 1 ps and/or having a fluence per pulse ranging between 0.001 and 10 J/cm2.

* * * * *